US011091529B2

(12) United States Patent
Bielicki et al.

(10) Patent No.: US 11,091,529 B2
(45) Date of Patent: Aug. 17, 2021

(54) PEPTIDES HAVING REDUCED TOXICITY THAT STIMULATE CHOLESTEROL EFFLUX

(71) Applicant: The Regents of the University of California, Oakland, CA (US)

(72) Inventors: John K. Bielicki, San Ramon, CA (US); Jan Johansson, San Ramon, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/511,623

(22) PCT Filed: Sep. 14, 2015

(86) PCT No.: PCT/US2015/050020
§ 371 (c)(1),
(2) Date: Mar. 15, 2017

(87) PCT Pub. No.: WO2016/044177
PCT Pub. Date: Mar. 24, 2016

(65) Prior Publication Data
US 2017/0283480 A1    Oct. 5, 2017

Related U.S. Application Data

(60) Provisional application No. 62/051,673, filed on Sep. 17, 2014.

(51) Int. Cl.
| | |
|---|---|
| A61K 38/16 | (2006.01) |
| C07K 14/705 | (2006.01) |
| A61K 47/54 | (2017.01) |
| A61K 38/17 | (2006.01) |
| A61K 38/00 | (2006.01) |

(52) U.S. Cl.
CPC .......... *C07K 14/705* (2013.01); *A61K 38/177* (2013.01); *A61K 47/544* (2017.08); *A61K 38/00* (2013.01)

(58) Field of Classification Search
None
See application file for complete search history.

(56) References Cited

U.S. PATENT DOCUMENTS

| | | |
|---|---|---|
| 8,119,590 B2 | 2/2012 | Bisgaier et al. |
| 8,415,293 B2 | 4/2013 | Bielicki et al. |
| 2005/0202532 A1 | 9/2005 | Bielicki et al. |
| 2012/0329703 A1* | 12/2012 | Bielicki ................. A61P 29/00 514/1.9 |
| 2014/0287994 A1 | 9/2014 | Bielicki et al. |

FOREIGN PATENT DOCUMENTS

| | | | | |
|---|---|---|---|---|
| WO | WO-2008115303 A2 * | 9/2008 | ......... | C07K 14/4703 |

OTHER PUBLICATIONS

Uniprot Accession No. Q75DT7 (accessed May 8, 2019 at URL uniprot.org/uniprot/Q75DT7; pp. 1-3) (Year: 2019).*
Bielicki et al., "A New HDL Mimetic Peptide That Stimulates Cellular Cholesterol Efflux with High Efficiency Greatly Reduces Atherosclerosis in Mice," *Journal of Lipid Research*, vol. 51, pp. 1496-1503 (Jan. 2010).
International Search Report from PCT/US2015/050020 dated Feb. 16, 2016, 4 pages.

* cited by examiner

*Primary Examiner* — Julie Ha
*Assistant Examiner* — Kristina M Hellman
(74) *Attorney, Agent, or Firm* — Kilpatrick Townsend & Stockton, LLP

(57) ABSTRACT

The present invention provides a family of non-naturally occurring polypeptides having cholesterol efflux activity that parallels that of full-length apolipoproteins (e.g., Apo AI and Apo E), and having high selectivity for ABCA1 that parallels that of full-length apolipoproteins. Further, the peptides of the invention have little or no toxicity when administered at therapeutic and higher doses. The invention also provides compositions comprising such polypeptides, methods of identifying, screening and synthesizing such polypeptides, and methods of treating, preventing or diagnosing diseases and disorders associated with dyslipidemia, hypercholesterolemia, or inflammation; or diseases involving abnormal glucose metabolism, e.g., diabetes, metabolic syndrome; or Alzheimers Disease or frontotemporal dementia.

16 Claims, 3 Drawing Sheets
Specification includes a Sequence Listing.

Figure 3

ATI-5261 analogs (all lysine and partial salt-bridge inversions)

| | | |
|---|---|---|
| ATI-5261 | EVRSKLEEWFAAFREFAEEFLARL | 24-mer ATI-5261 (no KS) |
| T5766-5 | EVRSKLEEWFAAFREFAEEFLARLNS | K25→N |
| T5594-4 | EVRSKLEEWFAAFKEFAEEFLAKLKS | R3,14,23→K |
| T5594-5 | EVESKLREWFAAFKEFAEEFLARLKS | R3,14→E; E7,18→R |
| T5594-6 | EVESKLREWFAAFREFAEEFARREFLARLKS | R3,14→E; E7,18→R |
| T5594-7 | EVESKLREWFAAFREFAEEFLARLKS | R3E; E7R |

Serum clinical markers – 4 hour post treatment

| | ALT (IU/L) | AST (IU/L) | TG (mg/dl) | FC (mg/dl) | NEFA (mg/dl) |
|---|---|---|---|---|---|
| PBS | 57±3 | 80±8 | 37±1 | 21±3 | 0.69±0.05 |
| ATI-5261 | 242±76 | 3391±1165 | 1671±1092 | 105±8 | 0.77±0.25 |
| T5766-5 | 158±43 | 2065±772 | 1682±180 | 95±5 | 0.59±0.14 |
| T5594-4 | 47±7 | 280±44 | 1642±383 | 163±16 | 0.76±0.27 |
| T5594-5 | 130±12 | 1858±187 | 1876±400 | 95±4 | 0.63±0.16 |
| T5594-6 | 238±16 | 4321±652 | 2263±21 | 110±4 | 1.10±0.28 |
| T5594-7 | 185±40 | 2349±487 | 2166±173 | 115±8 | 0.69±0.08 |

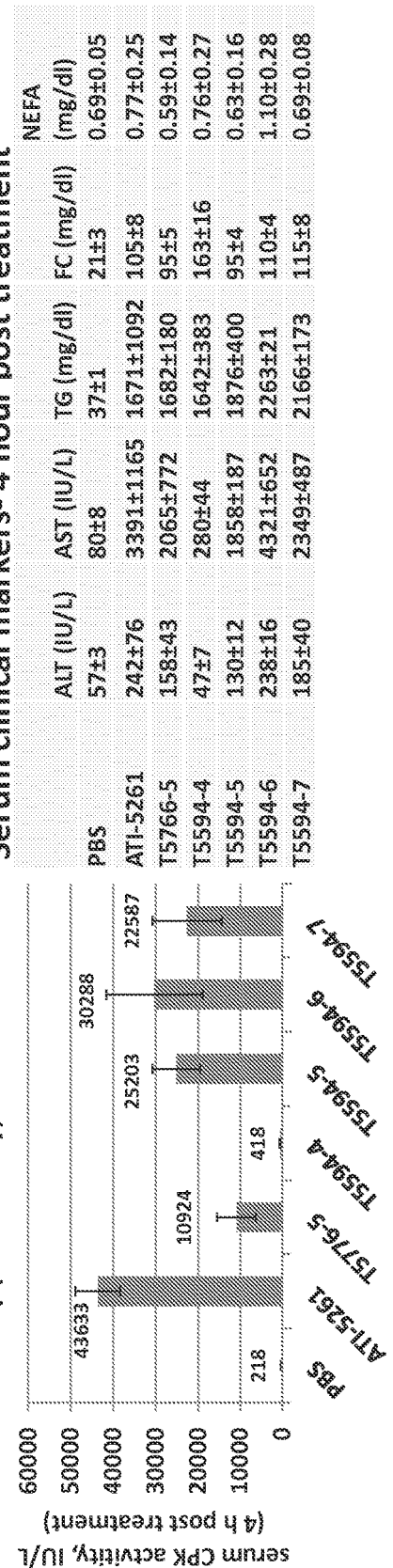

A  Muscle toxicity (CPK activity)

B  Cholesterol efflux activity

PEPTIDES HAVING REDUCED TOXICITY THAT STIMULATE CHOLESTEROL EFFLUX

CROSS-REFERENCE TO RELATED APPLICATIONS

This application is the U.S. National Stage of PCT/US2015/050020, filed Sep. 14, 2015, which claims priority benefit of U.S. Provisional Application No. 62/051,673, filed Sep. 17, 2014, each of which is herein incorporated by reference.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy and Grant No. HL085791 awarded by the National Institutes of Health. The Government has certain rights in this invention.

REFERENCE TO SUBMISSION OF A SEQUENCE LISTING

The Sequence Listing written in file 077429 1036546 SUB SEQ.TXT, created on Apr. 17, 2018, 13,810 bytes, machine format IBM-PC, MS-Windows operating system, is hereby incorporated by reference in its entirety for all purposes.

BACKGROUND OF THE INVENTION

Elevated levels of plasma HDL cholesterol are associated with reduced risk of atherosclerosis (Gordon et al., "High Density Lipoprotein As A Protective Factor Against Coronary Heart Disease," *Am. J. Med.*, 62:707-14 (1977)). The beneficial effects of HDL are related, in part, to activity in mediating the anti-atherogenic reverse cholesterol transport (RCT) pathway. RCT involves the transport of cholesterol from peripheral macrophages to the liver for excretion of sterol in feces (Lewis et al., "New Insights Into The Regulation of HDL Metabolism and Reverse Cholesterol Transport," *Circ. Res.*, 96:1221-32 (2005)). The rate-limiting step of RCT involves stimulation of cholesterol efflux from macrophages, mediated by native apolipoproteins such as Apo A-I and Apo E. This process of cholesterol efflux generates nascent HDL and requires the ATP-binding cassette transporter A1 (ABCA1) or else atherosclerosis is developed (Calpe-Berdiel et al., "Direct Evidence In Vivo of Impaired Macrophage-Specific Reverse Cholesterol Transport in ATP-Binding Cassette Transporter A1-Deficient Mice," *Biochim. Biophys. Acta.*, 1738(1-3):6-9 (2005).

The clinical importance of HDL has sparked interest in the development of strategies to manipulate RCT for therapeutic purposes. Peptides have been identified that can stimulate cholesterol efflux in vivo (see, e.g., WO 2008/115303 and WO 2009/155366). These peptides are characterized by alpha helices having a polar and non-polar surface and an alignment of acidic amino acids residues. However, in some contexts, these peptides have exhibited toxicity when administered at very high pharmacological doses. Accordingly, there is a need to provide improved peptides that have reduced toxicity. The present invention fulfills this need.

SUMMARY OF SOME ASPECTS OF THE INVENTION

The present invention relates to peptides that have cholesterol efflux activity and that have superior properties in terms of cytotoxicity profile. In some embodiments, a peptide of the invention has one or more salt bridge inversions in comparison to a reference sequence EVRSKLEEWLAALRELAEELLARL (SEQ ID NO:31). (See, also, PCT application PCT/US2014/029232, the entire contents of which is incorporated by reference herein for all purposes.) In some embodiments, salt bridges occur between residues 1 and 5, 3 and 7, 14, and 18, and 19 and 23, as determined with reference to SEQ ID NO:31. In other embodiments, a peptide of the invention has one or more salt bridge inversions in comparison to a reference sequence LRALLEEALERLAALWEELKSRVE (SEQ ID NO:32). In some embodiments, salt bridges occur between residues 2 and 6, 7 and 11, 18 and 22, and 20 and 24, as determined with reference to SEQ ID NO:32. In a salt bridge inversion, the acidic and positively charged residues are inverted at the noted positions. Thus, in SEQ ID NO:31, in one salt bridge inversion, the acidic residue and the positively charged residue at position 1 and 5 are inverted. In another salt bridge inversion, the positively charged residue at position 3 and the acidic residue at position 7 are inverted. In another salt bridge inversion, the positively charged residue at position 14 and the acidic residue at position 18 are inverted. In another salt bridge inversion, the acid residue at position 19 and the positively charged residue at position 23 are inverted. Similarly, in SEQ ID NO:32, in one salt bridge inversion, the acidic residue and the positively charged residue at position 24 and 20 are inverted. In another salt bridge inversion, the positively charged residue at position 22 and the acidic residue at position 18 are inverted. In another salt bridge inversion, the positively charged residue at position 11 and the acidic residue at position 7 are inverted. In another salt bridge inversion, the acid residue at position 6 and the positively charged residue at position 2 are inverted. A peptide of the invention may have one, two, three, or four salt bridge inversions as determined with reference to SEQ ID NO:31 or SEQ ID NO:32.

The invention also encompasses variants of SEQ ID NO:31 or 32 that comprise one or more salt bridge inversions and additional amino acid substitutions relative to SEQ ID NO:31 or SEQ ID NO:32. The amino acid residues involved in the salt bridge inversions need not be the specific amino acid shown in SEQ ID NO:31 or 32. Thus, where E in SEQ ID NO:31 or 32 is involved in a salt bridge, any acidic residue, such as D, may substitute for E. Similarly, where R in SEQ ID NO:31 or 32 is involved in a salt bridge, any positively charged residue, e.g., K, may substitute for R; and where K in SEQ ID NO:31 or 32 is involved in a salt bridge, any positively charged residue, e.g., R, may substitute for K.

A peptide of the invention may also comprise amino acid substitutions at positions, determined with reference to SEQ ID NO:31 or SEQ ID NO:32, that do not participate in salt bridges.

In typical embodiments, a peptide of the invention comprises a hydrophobic residue at each of positions 2, 6, 9, 10, 12, 13, 16, 17, 20, 21, and 24 as determined with reference to SEQ ID NO:31. In some embodiments, four, five, six, seven, or all eight of residues at positions 2, 6, 10, 13, 16, 17, 20, 21, and 24 are aliphatic residues. In some embodiments, the aliphatic residues are independently selected from the group consisting of L, V, A, and I. In some embodiments, the aliphatic residue at position 10, 13, 16, and 20 is independently selected from the group consisting of L, I, and V. In some embodiments, the aliphatic residue at position 10, 13, 16, and 20 is I or the aliphatic residue at position 10, 13, 16, and 20 is L. In some embodiments, a peptide of the invention comprises a residue independently selected from S, T, G, A, and Y, or an analog thereof, at position 4, 11, and 22. In some embodiments, a peptide of the invention comprises a charged residue at position 15 and position 8. In some embodiments, the peptide comprises a residue independently selected from D, E, R, and K at position 15 and position 8. In some embodiments, the peptide comprises D or E at position 15 and position 8. In some embodiments in which positions 3, 14, or 23 is not inverted in a salt bridge inversion relative to SEQ ID NO:31, the peptide comprises an uncharged residue, e.g., citrulline, or Q, N, Y, W, A, I, L, or V, at that position.

In typical embodiments, a peptide of the invention comprises a hydrophobic residue at each of positions 23, 19, 16, 13, 15, 12, 9, 8, 5, 4, and 1 as determined with reference to SEQ ID NO:32. In some embodiments, four, five, six, seven, or all eight of residues at positions 23, 19, 16, 12, 9, 8, 5, 4, and 1 are aliphatic residues. In some embodiments, the aliphatic residues are independently selected from the group consisting of L, V, A, and I. In some embodiments, the aliphatic residue at position 15, 12, 9, and 5 is independently selected from the group consisting of L, I, and V. In some embodiments, the aliphatic residue at position 15, 12, 9, and 5 is I or the aliphatic residue at position 15, 12, 9, and 5 is L. In some embodiments, a peptide of the invention comprises a residue independently selected from S, T, G, A, and Y, or an analog thereof, at position 21, 14, and 3. In some embodiments, a peptide of the invention comprises a charged residue at position 10 and 17. In some embodiments, the peptide comprises a residue independently selected from D, E, R, and K at position 10 and 17. In some embodiments, the peptide comprises D or E at position 10 and 17. In some embodiments in which positions 22, 11, or 2 is not inverted in a salt bridge inversion relative to SEQ ID NO:32, the peptide comprises an uncharged residue, e.g., citrulline, or Q, N, Y, W, A, I, L, or V, at that position.

In some embodiments, a peptide of the invention may have one, two, three, or four amino acids deleted or inserted, when determined with reference to SEQ ID NO:31 or 32. In some embodiments, a peptide of the invention may have 1 or 2 amino acids deleted at the N-terminus or C-terminus, e.g., the carboxy terminus, as determined with reference to SEQ ID NO:31 or 32.

A polypeptide of the present invention has cholesterol efflux activity and/or has ABCA1 stabilizing activity. In yet another embodiment, a polypeptide of the present invention protects a phospholipids from oxidation by an oxidizing agent (i.e., the polypeptide has anti-oxidant activity). In still another embodiment, a polypeptide of the present invention has anti-inflammatory activity, including inhibition of adhesion molecules. In another embodiment, administration of a polypeptide of the invention lowers LDL and/or has favorable effects on glucose control, i.e., glucose-lowering effects. In some embodiments, a peptide of the invention treats or prevents symptoms of Alzheimer's disease or frontotemporal dementia. In some embodiments, a polypeptide of the present invention comprises each of these activities.

In a further aspect, the invention provides pharmaceutical compositions comprising at least one peptide of the invention as described herein and a pharmaceutically acceptable carrier or excipient. In some embodiments, the pharmaceutical compositions comprise an additional therapeutic agent (e.g., a statin such as atorvastatin, lovastatin, pravastatin, simvastatin, fluvastatin, or rosuvastatin; a bile acid binder such as cholestyramine or colestipol; a Nieman-Pick C1-Like 1 sterol transporter channel inhibitor such as Ezetimibe; a platelet clumping inhibitor such as aspirin, ticlopidine, or clopidogrel, niacin/nicotinamide, a PPAR activator, Vitamin E, or combinations thereof, for treating a disease or disorder associated with cholesterol efflux (e.g., cardiovascular disease).

In another aspect, the invention provides peptidomimetics of the polypeptides disclosed herein, wherein the peptidomimetic is an analog peptide, e.g., a retro-inverso analog or retro-enantio analog; or surrogate peptide having a non-amide backbone. In yet another embodiment, the analog is a trans-olefin surrogate peptide or derivative. In some embodiments, a peptide of the invention can comprise other back-bone modifications. Such peptide analogs or surrogates can further comprise a protecting group as described herein and, preferably, a protecting group at both the amino and carboxyl termini.

In a further aspect, the present invention provides a composition comprising a polypeptide of the present invention as described herein, e.g., a polypeptide comprising any one of SEQ ID NOs:1-30, or variants thereof, or a peptidomimetic thereof complexed with a lipid. In one embodiment, the lipid is a phospholipid. In another embodiment, the phospholipids is 1-palmitoyl-2-oleoyl-sn-glycerol-3-phosphatidylcholine ("POPC"). In yet another embodiment, the composition further comprises a pharmaceutically acceptable carrier.

Yet another aspect of the invention provides methods of mediating cholesterol efflux in a mammalian subject (e.g., a primate such as a human, monkey, or chimpanzee; or a rodent such as a rat or mouse) by administering at least one polypeptide or peptidomimetic described herein to the subject. Those of skill in the art will appreciate that a nucleic acid encoding such a polypeptide (or peptidomimetic) can be administered to the subject in lieu of administering the polypeptide (or peptidomimetic). The present invention provides such nucleic acids. Based on their cholesterol efflux activity, the polypeptides and peptidomimetics of the present invention can be advantageously used to treat, ameliorate or prevent a disease or condition associated with dyslipidemia, hypercholesterolemia, abnormal glucose metabolism, Alzheimer's Disease, frontotemporal dementia, and inflammation.

Still another aspect of the present invention provides methods for treating or preventing a symptom of atherosclerosis in a mammal by administering at least one polypeptide or peptidomimetic described herein to the subject. Again, those of skill in the art will appreciate that a nucleic acid encoding such a polypeptide (or peptidomimetic) can be administered to the subject in lieu of administering the polypeptide (or peptidomimetic). Such nucleic acids are provided by the present invention. In one embodiment of this method, the mammal is a mammal diagnosed as having one or more symptoms of atherosclerosis. In another embodiment, the mammal is diagnosed as at risk for atherosclerosis. Preferably, the mammal is a human, but can also be a non-human animal. In one embodiment, the polypeptide comprises an amino acid sequence of any one of SEQ ID NOs:1-30 or a variant thereof as described herein.

In another related embodiment, the methods further comprise administering at least one additional therapeutic agent. Examples of such therapeutic agents include, but are not limited to, agents that treat abnormalities of glucose metabolism, e.g., anti-diabetic agents, agents that treat Alzheimer's disease and/or frontotemporal dementia, an antibody, an enzyme inhibitor, an antibacterial agent, an antiviral agent, a steroid, a non-steroidal anti-inflammatory agent, an antimetabolite, a cytokine, or a soluble cytokine receptor. The enzyme inhibitor may be a protease inhibitor or a cyclooxygenase inhibitor. The additional agent may be added as a part of a pharmaceutical composition, or may be administered concomitantly or within a time period when the physiological effect of the additional agent overlaps with the physiological effect of the polypeptide(s) or peptidomimetic(s) of the present invention. For example, more specifically, an additional agent may be administered concomitantly one week, several days, 24 hours, 8 hours, or immediately before the administration of the polypeptide(s) or peptidomimetic(s). Alternatively, an additional agent may, for example, be administered one week, several days, 24 hours, 8 hours, or immediately after the administration of the polypeptide(s) or peptidomimetic(s).

Yet another aspect of the present invention provides methods for stabilizing a vulnerable plaque, the method comprising administering to a mammal at least one polypeptide or peptidomimetic described herein. Again, those of skill in the art will appreciate that a nucleic acid encoding such a polypeptide can be administered to the subject in lieu of administering the polypeptide. Such nucleic acids are provided by the present invention. In one embodiment of this method, the mammal is a mammal diagnosed as having one or more vulnerable plaques. In another embodiment, the mammal is diagnosed as at risk for having a vulnerable plaque(s). Preferably, the mammal is a human, but can also be a non-human animal. In one embodiment, the polypeptide has an amino acid sequence of any one of SEQ ID NOs:1-30 or is a variant as described herein.

In another aspect of the present invention provides methods of lowering glucose levels in a patient having abnormal glucose metabolism, e.g., in a patient having diabetes, e.g., Type II or Type I diabetes, or metabolic syndrome, or pre-diabetes, the method comprising administering to a mammal at least one polypeptide or peptidomimetic described herein. Again, those of skill in the art will appreciate that a nucleic acid encoding such a polypeptide can be administered to the subject in lieu of administering the polypeptide. Such nucleic acids are provided by the present invention. In one embodiment of this method, the mammal is a mammal diagnosed as having abnormal glucose metabolism. In another embodiment, the mammal is diagnosed as at risk for having abnormal glucose metabolism. Preferably, the mammal is a human, but can also be a non-human animal. In one embodiment, the polypeptide has an amino acid sequence of any one of SEQ ID NOs:1-30 or is a variant thereof as described herein.

In another aspect of the present invention provides methods of preventing or treating a symptom of frontotemporal dementia, Alzheimer's Disease or Mild Cognitive Impairment, the method comprising administering to a subject at least one polypeptide or peptidomimetic described herein. Again, those of skill in the art will appreciate that a nucleic acid encoding such a polypeptide can be administered to the subject in lieu of administering the polypeptide. Such nucleic acids are provided by the present invention. In one embodiment of this method, the subject is diagnosed as having Alzheimer's Disease. In another embodiment, the subject is diagnosed as having Mild Cognitive Impairment. In some embodiments, the subject has an ApoE4 allele. In one embodiment, the polypeptide has an amino acid sequence of any one of SEQ ID NOs:1-30 or is a variant thereof as described herein.

The present invention also provides kits for treating or preventing a disease or condition associated with dyslipidemia, hypercholesterolemia, abnormal glucose metabolism, inflammation, and/or Alzheimer's Disease or frontotemporal dementia. In one embodiment, the present invention provides kits for treating or preventing a symptom of atherosclerosis, the kit comprising a container containing a polypeptide or peptidomimetic of the present invention. In one embodiment, the present invention provides kits for treating or preventing a disease associated with abnormal glucose metabolism, e.g., diabetes or metabolic syndrome, the kit comprising a container containing a polypeptide or peptidomimetic of the present invention. In one embodiment, the present invention provides kits for treating or preventing a symptom of Alzheimer's Disease, the kit comprising a container containing a polypeptide or peptidomimetic of the present invention. The kit can further comprise a pharmaceutically acceptable carrier.

In yet another aspect, the present invention provides use of at least one polypeptide or peptidomimetic of the present invention in the preparation of a medicament for mediating cholesterol efflux in a mammal, e.g., a human. In one embodiment, the polypeptide has an amino acid sequence of any one of SEQ ID NOs:1-30 or is a variant thereof as described herein.

In a further aspect, the present invention provides use of at least one polypeptide or peptidomimetic of the present invention in the preparation of a medicament for treating a symptom of atherosclerosis in a mammal, e.g., a human. In one embodiments, the polypeptide has an amino acid sequence of any one of SEQ ID NOs:1-30 or is a variant thereof as described herein.

In yet a further aspect, the present invention provides use of at least one polypeptide or peptidomimetic of the present invention in the preparation of a medicament for stabilizing a vulnerable plaque in a mammal, e.g., a human. In one embodiment, the polypeptide has an amino acid sequence of any one of SEQ ID NOs:1-30 or is a variant thereof as described herein.

In yet a further aspect, the present invention provides use of at least one polypeptide or peptidomimetic of the present invention in the preparation of a medicament for treating dyslipidemia or hypercholesterolemia in a patient. In one embodiment, the polypeptide has an amino acid sequence of any one of SEQ ID NOs:1-30 or is a variant thereof as described herein.

In yet a further aspect, the present invention provides use of at least one polypeptide or peptidomimetic of the present invention in the preparation of a medicament for decreasing blood glucose levels in a mammal, e.g., a human. In one embodiment, the polypeptide has an amino acid sequence of any one of SEQ ID NOs:1-30 or is a variant thereof as described herein.

In yet a further aspect, the present invention provides use of at least one polypeptide or peptidomimetic of the present invention in the preparation of a medicament for preventing or treating a symptom of frontotemporal dementia, Alzheimer's Disease or Mild Cognitive Impairment in a human. In one embodiment, the polypeptide has an amino acid sequence of any one of SEQ ID NOs:1-30 or is a variant thereof as described herein.

Another aspect of the invention provides an isolated nucleic acid encoding a polypeptide of the present invention, an expression vector comprising the nucleic acid, and a host cell comprising the expression vector.

A polypeptide and peptidomimetic of the invention is also useful as a research tool and/or diagnostic tool. For example, such a peptide can be used to identify subjects having reverse cholesterol deficient plasma and those subjects that are responders to reverse cholesterol treatment. Also, a polypeptide of the invention can be used to evaluate the anti-atherosclerotic potential of other compounds (including, e.g., peptidomimetics).

In addition, a polypeptide or peptidomimetic of the invention can be used for investigating lipoprotein-receptor interactions in animals and animal models, particularly when a polypeptide or peptidomimetic of the present invention is labeled (e.g., radioactive label, fluorescent label, etc.).

A polypeptide or peptidomimetic of the invention can also be used to identify appropriate animal models for elucidation of lipid metabolic pathways. For example, a polypeptide or peptidomimetic can be used to identify animal models and gene and/or drug interactions that have an effect on reverse cholesterol transport.

Other features, objects and advantages of the invention and its preferred embodiments will become apparent from a reading of the detailed description, examples, claims and figures that follow.

BRIEF DESCRIPTION OF THE DRAWINGS

FIG. 3—Toxic properties of lysine residues in ATI-5261—To test whether the cytotoxic response of ATI-5261 was preferentially linked to arginine or lysine residues, peptide analogs of ATI-5261 with lysine eliminations, R→K substitutions, or partial charge inversion were created. Panel A—Safety and TG elevating effects were evaluated by injecting (IP) peptides (300 mg/kg) into male, chow-fed C57Bl/6 mice. Values are means SD, n=4. Removal of lysine25 from C-terminal end of ATI-5261, by either ablation (T5766-5, SEQ ID NO:36) or amino acid substitution (K25→N, T5594-4, SEQ ID NO:37) greatly reduced muscle toxicity as judged by decreased CPK activity in plasma (left panel), suggesting lysine residues promote toxicity. Peptides with either all lysine residues (i.e. R→K substitutions, T5594-5, SEQ ID NO:38) or partial charged inversion (T5594-6, SEQ ID NO:39, T5594-7, SEQ ID NO:40) also displayed cytotoxic and TG elevating activity, consistent with role of either lysine or arginine in mediating negative effects of the peptides. Panel B-ABCA1-dependent cholesterol efflux activity of peptides determined using J774 macrophages labeled with [3H]cholesterol. Results are expressed as the ABCA1 component of efflux. All peptides were functional and stimulated high-levels of cholesterol efflux at a saturating concentration of 3 µg/ml, similar to that seen using the parent ATI-5261 peptide.

DETAILED DESCRIPTION OF THE INVENTION

Definitions

Figure 1:
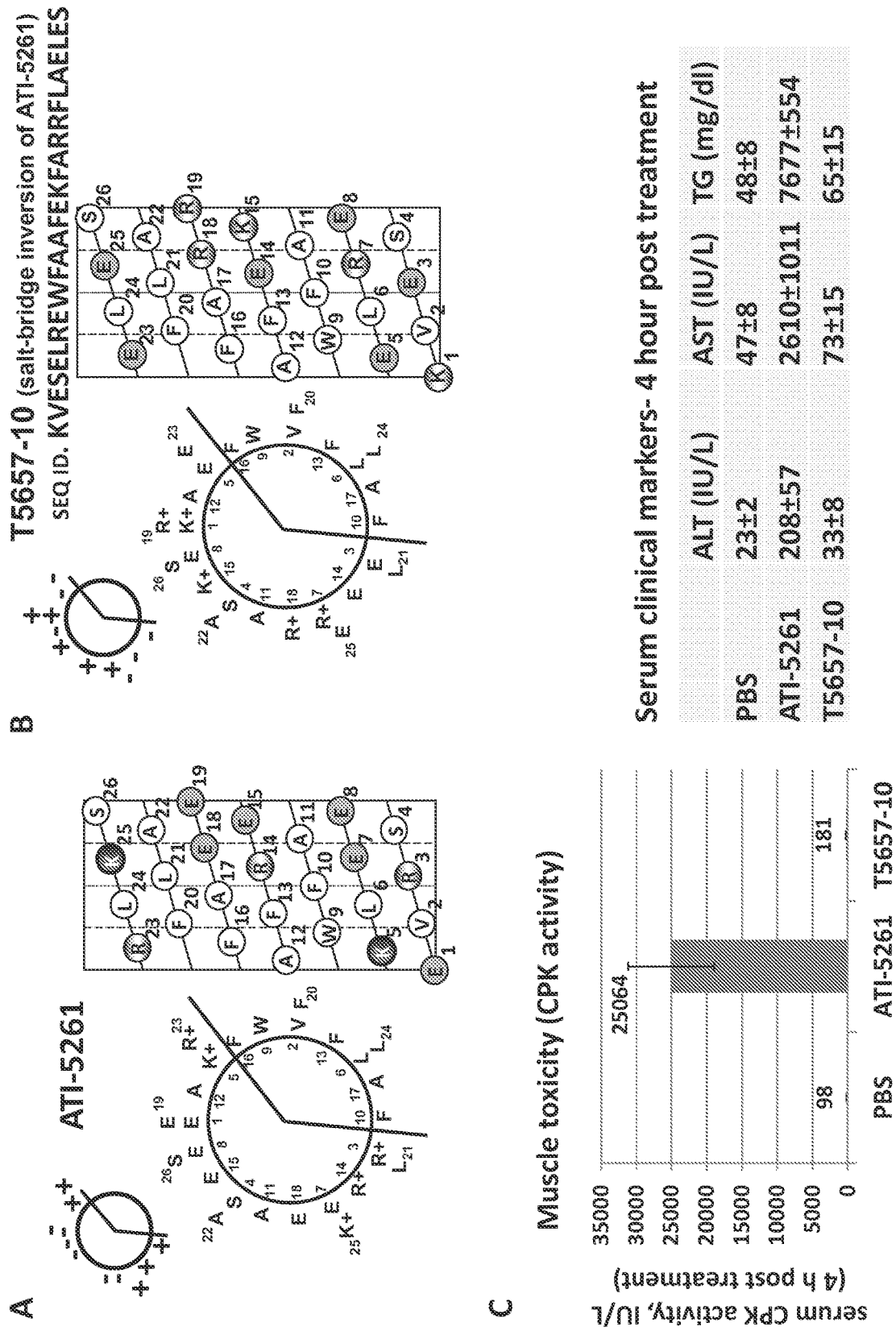
FIG. 1—Evidence that positively charged amino acids associated with Class A α-helix structure contribute to the toxic effects of ATI-5261 (SEQ ID NO:33). Aromatic F residues in ATI-5261 promote toxicity, which suggests that interactions of ATI-5261 with cellular membranes may be involved. Since the position of positively charged amino acids near the lipid-water interface of class A α-helices is thought to mediate membrane interactions, we tested whether inverting the positions of positive and negative residues within ATI-5261 lessened the toxic response of the peptide at high doses. Panel A—Helical-wheel and net diagrams of ATI-5261 showing the positions of positively charged lysine (K) and arginine (R) at the lipid interface of the amphipathic α-helix (i.e. helical wheel diagrams on left). Panel B—Peptide analogs of ATI-5261 with charge-inversions created by switching the positions of positive and negative amino acids within each of the peptides putative salt-bridges (shaded circles in helical-net diagram, i.e. positions i and i+4). Panel C— Figure showing that charge-inversion eliminates the cytotoxicity and TG elevating activity of ATI-5261. Male Chow-fed C57Bl/6 mice were injected IP with 300 mg/kg ATI-5261 and its charge inversion analog (T5657-10, SEQ ID NO:34). Plasma CPK, ALT, AST and TG (table) were assessed after 4 h. Values and means±SD, n=4. Moving the positively charged residues away from the lipid surface eliminated nearly all the cytotoxic and TG elevating activity of the ATI-5261, i.e. even in the presence of aromatic F residues. Thus the position of positively charged residues together with the presence of aromatic phenylalanine appears necessary to induce cytotoxicity, but each is not sufficient to induce such a response.

The term "ABC" or "ATP Binding Cassette" refers to multidomain membrane proteins, responsible for the controlled efflux and influx of allocrites (e.g. cholesterol) across cellular membranes. ABC proteins comprise four domains, with two transmembrane domains (TMDs) responsible for allocrite binding and transport and two nucleotide-binding domains (NBDs) responsible for coupling the energy of ATP hydrolysis to conformational changes in the TMDs. The family members include, e.g., ABCA1 and ABCA7 (see, e.g., Dean et al., *J. Lipid Res.*, 42:1007-1017 (2001)). ABCA1 is characterized in Denis et al., *J Biol Chem.*, 279(40):41529-36 (2004). ABCA1 plays a role in cholesterol efflux and is upregulated in cells that are exposed to cholesterol enriching conditions and is the defective molecule in Tangiers Disease (Brooks-Wilson et al., *Nat. Gen.*, 22:336-344 (1999); Bodzioch et al., *Nat. Gen.*, 22:347-351 (1999); Rust et al., *Nat. Gen.*, 22:352-355 (1999)). ABCA1 turns over rapidly and has a half-life of about 1 hour in the absence of a suitable stabilizer, such as an apolipoprotein (see, e.g., Wang et al., *J. Clin. Invest.*, 111:99-107 (2003)) ABCA1 sequences are set forth in Genbank Accession Nos.: AJ012376; NM_173076; NM_015657; NM_005502;

NP_005493; 095477. ABCA family members are reviewed in Broccardo et al., *Biochimica et Biophysica Acta*, 1461: 395-404 (1999).

The term "amphipathic alpha helix" or "amphipathic a helix" refers to a polypeptide sequence that can adopt a secondary structure that is helical with one surface, i.e., face, being polar and comprised primarily of hydrophilic amino acids (e.g., Asp, Glu, Lys, Arg, His, Gly, Ser, Thr, Cys, Tyr, Asn and Gln), and the other surface being a nonpolar face that comprises primarily hydrophobic amino acids (e.g., Leu, Ala, Val, Ile, Pro, Phe, Trp and Met) (see, e.g., Kaiser and Kezdy, *Ann. Rev. Biophys. Biophys. Chem.*, 16:561 (1987), and Science, 223:249 (1984)).

The polar face of an amphipathic α helix can, in some instances, display an "alignment of negatively charged amino acids" or "an alignment of acidic amino acids," i.e., a series of negatively charged or acidic amino acids (e.g., Asp and/or Glu) positioned approximately evenly (e.g., at about every one, two or three helical turns) within the polypeptide secondary structure. Amphipathic α helices play a role in both intra- and inter-molecular protein-protein interactions, and proteins and lipoproteins (e.g., including apolipoproteins) comprising amphipathic α helices have been postulated to play a role in lipid (e.g., HDL) transport and metabolism (see, e.g., Anantharamaiah et al., *Adv. Exp. Med. Biol.*, 285:131-40 (1991)). The structure and function of amphipathic α helices has been reviewed in, e.g., Segrest et al., *Proteins*, 8(2):103-17 (1990). In silico methods of identifying amphipathic α helices have been described by, e.g., Jones et al., *J. Lipid Res.*, 33(2):141-66 (1992). Multiple proteins comprising amphipathic α helices have been identified including, e.g., apolipoproteins and serum amyloid proteins.

The terms "cholesterol efflux" and "cholesterol efflux activity" refer to efflux of cholesterol from any cell type. For example, macrophage foam-cells in the artery wall release (i.e., export) cholesterol to appropriate acceptors, such as apolipoproteins and/or HDL. A compound that mediates cholesterol efflux enhances the release, i.e., movement, of cholesterol out of the cell and into the extracellular medium or compartment. Cholesterol efflux is often accompanied by or preceded by, i.e., follows, the efflux of phospholipids from cells. The coordinated release of both cholesterol and phospholipids produces HDL in the presence of a suitable lipid acceptor, e.g., apolipoprotein or peptide. Therefore, the processes of cholesterol- and phospholipid-efflux are linked and synonymous with one another. A compound that enhances the release of cholesterol from cells increases the amount of cholesterol and/or phospholipids appearing outside the cell by at least 25%, 50%, 75%, 100% or by at least 2-fold, 4-fold, 8-fold, 10-fold or more compared to the level of cholesterol efflux in the absence of the compound.

The term "ABCA stabilization activity" or "ABCA1 stabilization" refers to enhancing and/or extending the half-life of an ABCA protein by preventing its degradation. A compound that has ABCA1 stabilization activity will significantly delay the proteins degradation. This will produce an increase in cellular ABCA1 protein levels of at least 25%, 50%, 75%, 100% or at least 2-fold, 4-fold, 8-fold, 10-fold or higher compared to ABCA1 protein detected in the absence of the compound.

The term "anti-inflammatory activity" refers to prevention or reduction of inflammation. Inflammation will be recognized as playing a role in atherosclerosis development and associated with dyslipidemia, hypercholesterolemia and/or lipoprotein lipid oxidation as well as other diseases. The inflammatory response can be local, such as in the artery wall or brain or other extra-vascular tissues, and/or systemic. A peptide that has anti-inflammatory activity will decrease an inflammatory response as measured by a decrease in inflammatory mediators (e.g., adhesion molecules, cytokines and/or oxidized lipids) and/or a decrease in macrophages and/or macrophage activation in plaques and tissues, compared to in the absence of the peptide.

The term "antioxidant activity" refers to prevention or reduction of oxidation caused by reactive oxygen species (ROS) including, e.g., hydrogen peroxide ($H_2O_2$); hypochlorite ion (—OCl); hydroxyl radical (—OH); and the superoxide anion ($O_2$—). Many naturally occurring substances possess antioxidant activity. For example, apolipoproteins can inhibit lipid peroxidation, thus protecting phospholipid surfaces from lipophilic, as well as, water soluble free radical initiators (see, e.g., *Biochemistry*, 41:2089-2096 (2002)). In the context of this invention, a peptide with an antioxidant activity has an antioxidant activity that is at least 25%, 50%, 75%, 100% or at least 2-fold, 4-fold, 8-fold, 10-fold or more higher than the antioxidant activity in the absence of the peptide.

"Plaque stabilization," as used herein, refers to the stabilization of vulnerable plaques from risk of rupture or erosion by removing cholesterol from lipid rich plaques, including but not limited to, removal of cholesterol from foam cell macrophages.

"Reverse Cholesterol Transport (RCT)," as used herein, refers to the process of removing cholesterol from macrophage foam cells and the lipid rich plaque from the arterial wall, with subsequent transfer through plasma to the liver for uptake, processing and excretion as neutral sterols (cholesterol) or acidic sterols (hydroxylated cholesterol/bile) in feces. The efflux of cholesterol from macrophage foam cells is a requirement for RCT benefit in itself even though the cholesterol may be shifted to other less vulnerable adjacent cells. However, the further disposal of such cholesterol by transport in HDL-like particles to the liver for excretion is a favorable aspect of treatment. The RCT and plaque stabilizing effects are either conferred directly by the peptides, or the complexes that they naturally form with phospholipids in plasma and cells or, alternatively, apoA-I/HDL as the peptides bind to endogenous HDL particles, thereby changing their properties and making them more efficient to promote RCT.

A disease or disorder associated with "dyslipidemia" is any disease or disorder in which lipid metabolism is dis-regulated, due to alterations in tissue (i.e., blood) lipids and lipoprotein concentrations and/or aberrant mediation of cholesterol efflux or aberrant ABCA stabilization. Such diseases include, for example, heart disease, atherosclerotic lesions, stroke, Alzheimer's, and storage disorders.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. The amino acids may be neutral, positive or negative depending on the substituents in the side chain. "Neutral amino acid" means an amino acid containing uncharged side chain substituents. Examples of neutral amino acids include alanine, valine, leucine, isoleucine, proline, phenylalanine, tryptophan, methionine, glycine, serine, threonine and cysteine. "Positive amino acid" means an amino acid in which the side chain substituents are positively charged at physiological pH. Examples of positive amino acids include lysine, arginine and histidine. "Negative amino acid" means an amino acid in which the side chain substituents bear a net negative charge at physiological pH. Examples of negative amino acids include aspartic acid and glutamic acid. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium.

Such analogs have modified R groups (e.g., norleucine) or modified polypeptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acid is also meant to include -amino acids having L or D stereochemistry at the α-carbon. A more detailed description of amino acid as well as conservative amino acid substitutions is provided below in the section entitled "Polypeptides."

A "non-natural amino acid" is included in the definition of an amino acid and refers to an amino acid that is not one of the 20 common naturally occurring amino acids or the rare naturally occurring amino acids e.g., selenocysteine or pyrrolysine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids. The use of the term "peptide or peptidomimetic" in the current application merely emphasizes that peptides comprising naturally occurring amino acids as well as modified amino acids are contemplated.

"Stapling" or "hydrocarbon-stapling" as used herein introduces into a peptide at least two moieties capable of undergoing reaction to promote carbon-carbon bond formation that can be contacted with a reagent to generate at least one cross-linker between the at least two moieties. Stapling provides a constraint on a secondary structure, such as an alpha helix structure. The length and geometry of the cross-linker can be optimized to improve the yield of the desired secondary structure content. The constraint provided can, for example, prevent the secondary structure to unfold and/or can reinforce the shape of the secondary structure. A secondary structure that is prevented from unfolding is, for example, more stable.

A "stapled" peptide is a peptide comprising a selected number of standard or non-standard amino acids, further comprising at least two moieties capable of undergoing reaction to promote carbon-carbon bond formation, that has been contacted with a reagent to generate at least one cross-linker between the at least two moieties, which modulates, for example, peptide stability.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "identical" or percent "identity," in the context of two or more polypeptide sequences (or two or more nucleic acids), refer to two or more sequences or subsequences that are the same or have a specified percentage of amino acid residues or nucleotides that are the same e.g., 60% identity, preferably 65%, 70%, 75%, 80%, 85%, 90%, 1%, 92%, 93%, 94%, 95%, 96%, 97%, 98%, 99% or 100% identity over a specified region (such as the 24 amino acids of SEQ ID NO:31 or the 24 amino acids of SEQ ID NO:32, or the 24 amino acids of any one of SEQ ID NOS:1-30), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters are used. Alternatively, sequences may be aligned by hand to determine the percent identity.

The terms "numbered with reference to", or "corresponding to", or "determined with reference to" when used in the context of the numbering of a given amino acid residue, refers to the numbering of the residues of a specified reference sequence when the given amino acid sequence is compared to the reference sequence. Thus, a residue in a polypeptide "corresponds to" an amino acid at a position in SEQ ID NO:31 when the residue aligns with the amino acid in an alignment of SEQ ID NO:31 to the variant protein. The polypeptide that is aligned to the reference sequence need not be the same length as the reference sequence.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, polypeptide-nucleic acids (PNAs). Unless otherwise indicated, a particular nucleic acid sequence also encompasses "conservatively modified variants" thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.*, 260:2605-2608 (1985); Rossolini et al., *Mol. Cell. Probes*, 8:91-98 (1994)). The term nucleic acid is used interchangeably with gene, cDNA, mRNA, oligonucleotide, and polynucleotide.

As used herein, "ameliorates" means alleviate, lessen, or decrease the extent of a symptom or decrease the number of occurrences of episodes of a disease manifestation.

The term "preventing" is art-recognized, and when used in relation to a condition, such as recurrence or onset of a disease such as hypercholesterolemia or atherosclerosis, is well understood in the art, and includes administration of a composition which reduces the frequency of, or delays the onset of, symptoms of a medical condition in a subject relative to a subject which does not receive the composition.

As used herein, "treating" means either slowing, stopping or reversing the progression of the disorder or disease. In a preferred embodiment, "treating" means reversing the progression to the point of eliminating the disorder or disease.

As used herein, "inhibits" means that the amount is reduced as compared with the amount that would occur in a control sample. In a preferred embodiment, inhibits means that the amount is reduced by at least 50% or more, or even more preferably by more than 75% or even 100%.

A "subject," "patient" or "mammal" to be treated by the methods disclosed herein can mean either a human or non-human animal.

Polypeptides

The present invention provides a family of non-naturally occurring polypeptides that use the potent Reverse Cholesterol Transport (RCT) pathway to mediate cholesterol efflux. The polypeptides of the present invention typically comprise a peptide having the amino acid sequence of any one of SEQ ID NOS:1-30 or a non-naturally occurring peptide variant of the sequence. The peptides of the invention stimulate ABCA1-dependent cholesterol efflux with a molar potency similar to that of apolipoproteins (e.g., Apo A-I, Apo E, etc.). In addition to being potent and selective mediators of ABCA1-dependent cholesterol efflux, the polypeptides have little or no toxicity when administered at high doses. The polypeptides of the present invention also have ABCA stabilization activity, LDL-lowering activity, anti-oxidant activity as well as anti-inflammatory activity, can improve glucose metabolism, can treat symptoms of Alzheimer's Disease or have any combination of these activities and, preferably, all of these activities.

As used herein, the term "little or no toxicity" is used interchangeably with "little or no cytotoxicity" to refer to a level of cytotoxicity for a peptide of the invention administered at a high pharmacological that typically is essentially equivalent to that obtained using a control only, i.e., a vehicle such as PBS that does not contain the peptide. Toxicity can be measured in an in vitro or in vivo assay. For example, in a rat, mouse, or rabbit model in which a peptide is administered IP at a dose of 300 mg/kg a response 50% or more above PBS, and in some embodiments, 40%, 30%, or 20% above PBS is considered toxic.

As used herein, a "high pharmacological dose" refers to an amount that is above the therapeutic dose, e.g., at least two-fold to 10-fold higher. For example, using a rat, rabbit, or mouse model, a high pharmacological dose may range from 30 mg/kg to 300 mg/kg, or up to 500 mg/kg. In some embodiments, a high therapeutic dose in a rat, mouse or rabbit model to evaluate toxicity is 300 mg/kg.

Regarding amphipathic α-helix peptides, hydrophobic amino acids are concentrated on one side of the helix, usually with polar or hydrophilic amino acids on the other. This arrangement is common in alpha helices of apolipoproteins and globular proteins, where one face of the helix is oriented toward the hydrophobic core and one face is oriented toward the water-exposed surface. Different amino-acid sequences have different propensities for forming α-helical structure. Methionine, alanine, leucine, glutamate, and lysine all have especially high helix-forming propensities, whereas proline, glycine, tyrosine, and serine have relatively poor helix-forming propensities. Proline tends to break or kink helices because it cannot donate an amide hydrogen bond (having no amide hydrogen), and because its side chain interferes sterically. Its ring structure also restricts its backbone dihedral angle to the vicinity of −70°, which is less common in α-helices. One of skill understands that although proline may be present at certain positions in the sequences described herein, the presence of more than three prolines within the sequence would be expected to disrupt the helical structure. Accordingly, the polypeptides of the invention do not have more than three prolines, and commonly do not have more than two prolines present at positions in the alpha-helix forming sequence. Typically, when a proline is present in the sequence of a core helical structure of a peptide of the invention, e.g., a peptide variant of any one of SEQ ID NOS:1 to 30, it is present in only one position of the core helix sequence.

Representative amino acids that can be present in a variant of any one of SEQ ID NOS:1 to 15 at positions 2, 4, 6, 8, 9, 10, 11, 12, 13, 15, 16, 17, 20, 21, 22 or 24 are shown below. Residues at positions 1 and 5, 3 and 7, 14 and 18, and 19 and 23 participate in salt bridges in which one of the residues is an acidic amino acid, e.g., E or D; and the second residue is a positively charged, e.g., R or K, or in some embodiments, an uncharged amino acid, such as citrulline, or an A, V, L, I, F, W, M, P, G, S, T, C, Y, N, or Q residue. In some embodiments, the residue at position 15 and/or position 8 is an acidic residue. In some embodiments, the residue at position 15 and/or position 8 is a positively charged residue.

```
Postn¹  1 2 3 4 5 6 7 8 9 10 11 12 13 14 15 16 17 18 19 20 21 22 23 24

AA(s)   * A * S * A * E A  A  S  A  A  *  E  A  A  *  *  A  A  S  *  A
          V   T   V   D V  V  T  V  V     D  V  V        V  V  T     V
          L   G   L   R L  L  G  L  L     R  L  L        L  L  G     L
          I   A   I   K I  I  A  I  I     K  I  I        I  I  A     I
          F   Y   F     F  F  Y  F  F        F  F        F  F  Y     F
          W       W     W  W     W  W        W  W        W  W        W
          M       M     M  M     M  M        M  M        M  M        M
          P       P     P  P     P  P        P  P        P  P        P
```

In some embodiments, positions 2, 4, 6, 8, 9, 10, 11, 12, 13, 15, 16, 17, 20, 21, 22 or 24 in a variant of any one of SEQ ID NOS:1 to 15 may have a residue shown below and residues at positions 1 and 5, 3 and 7, 14 and 18, and 19 and 23 that participate in salt bridges in which one of the residues is an acidic amino acid, e.g., E or D; and the second residue is a positively charged, e.g., R or K, or in some embodiments, an uncharged amino acid, such as citrulline, or an A, V, L, I, F, W, M, P, G, S, T, C, Y, N, or Q residue. In some embodiments, the uncharged amino acid is citrulline or an analog thereof, or A, V, L, I, M, W, M, P, G, S, T, C, Y, N, or Q. In some embodiments, the uncharged residue is citrulline. In some embodiments, the uncharged residue is Q, N, Y, W, A, I, L, or V. In some embodiments, the uncharge residue is an aliphatic residue, such as A, I, L, or V.

```
Postn¹  1 2 3 4 5 6 7 8 9 10 11 12 13 14 15 16 17 18 19 20 21 22 23 24

AA(s)   * F * S * L * E W  F  A  A  F  *  E  F  F  *  *  F  L  A  *  L
          V       F   D L  L           L     D  L  A        L           F
          L       W   F W                 W     W  L        W           W
          I                                        W
          W
```

Representative amino acids that can be present in a variant of any one of SEQ ID NOS:16 to 30 at positions 23, 21, 19, 17, 16, 15, 14, 13, 12, 10, 9, 8, 5, 4, 3 or 1 are shown below. Residues at positions 24 and 20, 22 and 18, 11 and 7, and 6 and 2 participate in salt bridges in which one of the residues is an acidic amino acid, e.g., E or D; and the second residue is a positively charged, e.g., R or K, or in some embodiments, an uncharged amino acid, such as citrulline, or an A, V, L, I, F, W, M, P, G, S, T, C, Y, N, or Q residue. In some embodiments, the residue at position 10 and/or position 17 is an acidic residue. In some embodiments, the residue at position 10 and/or position 17 is a positively charged residue.

```
Postn¹  24 23 22 21 20 19 18 17 16 15 14 13 12 11 10 9 8 7 6 5 4 3 2 1

AA(s)   *  A  *  S  *  A  *  E  A  A  S  A  A  *  E A A * * A A S * A
           V     T     V     D  V  V  T  V  V     D V V     V V T   V
           L     G     L     R  L  L  G  L  L     R L L     L L G   L
           I     A     I     K  I  I  A  I  I     K I I     I I A   I
           F     Y     F        F  F  Y  F  F       F F     F F Y   F
           W           W        W  W     W  W       W W     W W     W
           M           M        M  M     M  M       M M     M M     M
           P           P        P  P     P  P       P P     P P     P
```

In some embodiments, 23, 21, 19, 17, 16, 15, 14, 13, 12, 10, 9, 8, 5, 4, 3 or 1 in any one of SEQ ID NOS:16 to 30 may have a residue shown below and residues at positions 24 and 20, 22 and 18, 11 and 7, and 6 and 2 that participate in salt bridges in which one of the residues is an acidic amino acid, e.g., E or D; and the second residue is a positively charged, e.g., R or K, or in some embodiments, an uncharged amino acid, such as citrulline, or an A, V, L, I, F, W, M, P, G, S, T, C, Y, N, or Q residue. In some embodiments, the uncharged amino acid is citrulline or an analog thereof, or A, V, L, I, M, W, M, P, G, S, T, C, Y, N, or Q. In some embodiments, the uncharged residue is citrulline. In some embodiments, the uncharged residue is Q, N, Y, W, A, I, L, or V. In some embodiments, the uncharged residue is an aliphatic residue, such as A, I, L, or V.

| Postn[1] | 24 | 23 | 22 | 21 | 20 | 19 | 18 | 17 | 16 | 15 | 14 | 13 | 12 | 11 | 10 | 9 | 8 | 7 | 6 | 5 | 4 | 3 | 2 | 1 |
|---|---|---|---|---|---|---|---|---|---|---|---|---|---|---|---|---|---|---|---|---|---|---|---|---|
| AA(s) | * | F | * | S | * | L | * | E | W | F | A | A | F | * | E | F | F | * | * | F | L | A | * | L |
|  |  | V |  |  |  | F |  | D | L | L |  |  | L |  | D | L | A |  |  | L |  |  |  | F |
|  |  | L |  |  |  | W |  | F | W |  |  |  | W |  |  | W | L |  |  | W |  |  |  | W |
|  |  | I |  |  |  |  |  |  |  |  |  |  |  |  |  |  | W |  |  |  |  |  |  |   |
|  |  | W |  |  |  |  |  |  |  |  |  |  |  |  |  |  |  |  |  |  |  |  |  |   |

A polypeptide of the present invention having cholesterol efflux activity comprises an amino acid sequence that is an amphipathic α-helix having a non-polar surface and a polar surface where the polar surface comprises charged and and uncharged amino acid residues at the lipid-water interface. In some embodiments, a peptide of the invention comprises an amino acid sequence of any one of reference sequences SEQ ID NOS:1-30, or variants thereof, wherein the variants comprises an amino acid sequence having at least 50%, typically at least 55%, at least 60%, at least 65%, at least 70%, at least 80%, at least 85%, at least 90%, or at least 95%, or greater identity to the reference sequence.

In some embodiments, the sequence has at least one salt bridge inversion relative to SEQ ID NO:31 and has at least 60% or at least 65% identity; or at least 70%, at least 75%, at least 80%, at least 85%, at least 90%, or at least 95% to any one of the following sequences SEQ ID NOs:1, 2, 3, or 4, each of which comprise a single salt bridge inversion relative to SEQ ID NO:31.

```
                                (SEQ ID NO: 1)
KVRSELEEWLAALRELAEELLARL (SEQ ID NO: 2)
EVESKLREWLAALRELAEELLARL (SEQ ID NO: 3)
EVRSKLEEWLAALEELARELLARL (SEQ ID NO: 4)
EVRSKLEEWLAALRELAERLLAEL
```

In some embodiments, the sequence has at least two salt bridge inversions relative to SEQ ID NO:31 and has at least 60% or at least 65% identity; or at least 70%, at least 75%, at least 80%, at least 85%, at least 90%, or at least 95% to any one of the following sequences SEQ ID NOs:5, 6, 7, 8, 9, or 10, each of which comprise two salt bridge inversions relative to SEQ ID NO:31.

```
                                (SEQ ID NO: 5)
KVESELREWLAALRELAEELLARL (SEQ ID NO: 6)
KVRSELEEWLAALEELARELLARL (SEQ ID NO: 7)
KVRSELEEWLAALRELAERLLAEL (SEQ ID NO: 8)
EVESKLREWLAALEELARELLARL (SEQ ID NO: 9)
EVESKLREWLAALRELAERLLAEL (SEQ ID NO: 10)
EVRSKLEEWLAALEELARRLLAEL
```

In some embodiments, the sequence has at least three salt bridge inversions relative to SEQ ID NO:31 and has at least 60% or at least 65% identity; or at least 70%, at least 75%, at least 80%, at least 85%, at least 90%, or at least 95% to any one of the following sequences SEQ ID NOs:11, 12, 13, or 14, each of which comprise three salt bridge inversions relative to SEQ ID NO:31.

```
                                (SEQ ID NO: 11)
KVESELREWLAALEELARELLARL (SEQ ID NO: 12)
KVESELREWLAALRELAERLLAEL (SEQ ID NO: 13)
KVRSELEEWLAALEELARRLLAEL (SEQ ID NO: 14)
KVESKLREWLAALEELARRLLAEL
```

In some embodiments, the sequence has four salt bridge inversions relative to SEQ ID NO:31 and has at least 60% or at least 65% identity; or at least 70%, at least 75%, at least 80%, at least 85%, at least 90%, or at least 95% to SEQ ID NO:15, which comprises four salt bridge inversions relative to SEQ ID NO:31.

```
                                (SEQ ID NO: 15)
RVESELREWLAALEELARRLLAEL
```

In some embodiments, the sequence has at least one salt bridge inversion relative to SEQ ID NO:32 and has at least 60% or at least 65% identity; or at least 70%, at least 75%, at least 80%, at least 85%, at least 90%, or at least 95% to any one of the following sequences SEQ ID NOs:16, 17, 18, or 19, each of which comprise a single salt bridge inversion relative to SEQ ID NO:32.

```
                                (SEQ ID NO: 16)
LRALLEEALERLAALWEELESRVK (SEQ ID NO: 17)
LRALLEEALERLAALWERLKSEVE (SEQ ID NO: 18)
LRALLERALEELAALWEELKSRVE (SEQ ID NO: 19)
LEALLREALERLAALWEELKSRVE
```

In some embodiments, the sequence has at least two salt bridge inversions relative to SEQ ID NO:32 and has at least 60% or at least 65% identity; or at least 70%, at least 75%, at least 80%, at least 85%, at least 90%, or at least 95% to any one of the following sequences SEQ ID NOs:20, 21, 22, 23, 24, or 25, each of which comprise two salt bridge inversions relative to SEQ ID NO:32.

```
                                (SEQ ID NO: 20)
LRALLEEALERLAALWERLESEVK (SEQ ID NO: 21)
LRALLERALEELAALWEELESRVK
```

-continued

LEALLREALERLAALWEELESRVK (SEQ ID NO: 22)

LRALLERALEELAALWERLKSEVE (SEQ ID NO: 23)

LEALLREALERLAALWERLKSEVE (SEQ ID NO: 24)

LEALLRRALEELAALWEELKSRVE (SEQ ID NO: 25)

In some embodiments, the sequence has at least three salt bridge inversions relative to SEQ ID NO:32 and has at least 60% or at least 65% identity; or at least 70%, at least 75%, at least 80%, at least 85%, at least 90%, or at least 95% to any one of the following sequences SEQ ID NOs:26, 27, 28, or 29, each of which comprise three salt bridge inversions relative to SEQ ID NO:32.

LRALLERALEELAALWERLESEVK (SEQ ID NO: 26)

LEALLREALERLAALWERLESEVK (SEQ ID NO: 27)

LEALLRRALEELAALWEELESRVK (SEQ ID NO: 28)

LEALLRRALEELAALWERLKSEVE (SEQ ID NO: 29)

In some embodiments, the sequence has four salt bridge inversions relative to SEQ ID NO:32 and has at least 60% or at least 65% identity; or at least 70%, at least 75%, at least 80%, at least 85%, at least 90%, or at least 95% to SEQ ID NO:30, which comprises four salt bridge inversions relative to SEQ ID NO:32.

LEALLRRALEELAALWERLESEVK (SEQ ID NO: 30)

In some embodiments, when a peptide has at least one salt bridge inversion as determined with reference to SEQ ID NO:31, the peptide may have at least one citrulline or analog of citrulline; or an uncharged residue, that is present at the lipid-water interface at a position that is not involved in the salt bridge inversion, for example at position 3, 14, or 23 as numbered with reference to SEQ ID NO:31. For example, for a peptide having one salt bridge between 1 and 5 in which there is a positively charged amino acid at position 1 and an acidic residue at position 5, one or two of positions 3, 14, or 23 9 may be citrulline or a citrulline analog; or an uncharged residue such as I, L, M or V. In some embodiments, the uncharged residue is L. Similarly, a peptide having a salt bridge between positions 3 and 7, where 3 is an acidic residue and 7 is a positively charged residue, may have a citrulline, or citrulline analog, at position 14 and/or position 23; or an uncharged residue, such as I, L, M or V at position 14 and/or position 23. In some embodiments, the uncharged residue is L. A peptide having a salt bridge between positions 14 and 18, wherein 14 is an acidic residue and 18 is a positively charged residue, may have a citrulline or citrulline analog at position 3 and/or 23; or an uncharged residue, such as I, L, M, or V at position 3 and/or 23. In some embodiments, the uncharged residue is L. A peptide having a salt bridge between positions 19 and 23, where position 19 is a positively charged residue and position 23 is an acidic residue, may have a citrulline or citurlline analog at position 3 and/or 14; or an uncharged residue, such as I, L, M, or V, at position 3 and/or 14. In some embodiments, the uncharged residue is L.

In some embodiments, when a peptide has at least one salt bridge inversion as determined with reference to SEQ ID NO:32, the peptide may have at least one citrulline or analog of citrulline; or an uncharged residue, that is present at the lipid-water interface at a position that is not involved in the salt bridge inversion, for example at position SEQ ID NO:32. For example, for a peptide having a salt bridge between 24 and 20 in which there is a positively charged amino acid at position 24 and an acidic residue at position 20, one or two of positions 21, 11, or 2, may be citrulline or a citrulline analog; or an uncharged residue such as I, L, M or V. In some embodiments, the uncharged residue is L. Similarly, a peptide having a salt bridge between positions 22 and 18, where 22 is an acidic residue and 18 is a positively charged residue, may have a citrulline, or citrulline analog, at position 11 and/or position 2; or an uncharged residue, such as I, L, M or V at position 11 and/or position 2. In some embodiments, the uncharged residue is L. A peptide having a salt bridge between positions 11 and 7, wherein 11 is an acidic residue and 7 is a positively charged residue, may have a citrulline or citrulline analog at position 21 and/or 2; or an uncharged residue, such as I, L, M, or V at position 21 and/or 2. In some embodiments, the uncharged residue is L. A peptide having a salt bridge between positions 6 and 2, where position 6 is a positively charged residue and position 2 is an acidic residue, may have a citrulline or citurlline analog at position 21 and/or 11; or an uncharged residue, such as I, L, M, or V, at position 21 and/or 11. In some embodiments, the uncharged residue is L.

In some embodiments, a variant comprises a hydrophobic amino acid, typically an aliphatic amino acid, at at least one, or at least two, three, four, five, six, seven, eight, nine, or ten of positions 2, 6, 9, 10, 13, 16, 17, 20, 21, 22, and 24 as determined with reference to SEQ ID NO:31, or any one of SEQ ID NOS:1 to 15. In some embodiments, a variant of any one of SEQ ID NOS:1 to 15 comprises no more than three or no more than two, or no more than one aromatic amino acids. In some embodiments a variant comprises an aliphatic residue at each of positions 2, 6, 10, 13, 16, 20, 21, and 24. In some embodiments, the aliphatic amino acid is L, V, A, or I. In some embodiments, a peptide of the invention comprises the same aliphatic amino acid at each of positions 10, 13, 16, and 20. In some embodiments, the same aliphatic amino acid at each of positions 10, 13, 16, and 20 is a branched chain aliphatic amino acid. In some embodiments, the same aliphatic amino acid at each of positions 10, 13, 16, and 20 is selected from the group consisting of L, I, or V. In some embodiments, the amino acid residue at position 10, 13, 16, and 20 is I. In some embodiments, the amino acid residue at position 10, 13, 16, and 20 is L. In some embodiments, the aliphatic amino acid residue at position 2 is V or L. In some embodiments, the aliphatic amino acid residue at position 2 is V and the aliphatic amino acid residue at position 10, 13, 16, and 20 is I or L. In some embodiments, the aliphatic amino acid at position 2 is V, the aliphatic amino acid at position 6, 21, and 24 is L, and the aliphatic amino acid residue at position 10, 13, 16, and 20 is I or L. In some embodiments, a variant comprises A at positions 11 and 12.

In some embodiments, a variant comprises a hydrophobic amino acid, typically an aliphatic amino acid, at least one, or at least two, three, four, five, six, seven, eight, nine, or ten of positions 23, 19, 16, 15, 12, 9, 8, 5, 4, 3, and 1 as determined with reference to SEQ ID NO:32, or any one of SEQ ID NOS:16 to 30. In some embodiments, a variant of any one of SEQ ID NOS:16 to 30 comprises no more than three or no more than two, or no more than one aromatic amino acids. In some embodiments a variant comprises an aliphatic residue at each of positions 23, 19, 15, 12, 9, 5, 4, and 1. In some embodiments, the aliphatic amino acid is L, V, A, or I. In some embodiments, a peptide of the invention comprises the same aliphatic amino acid at each of positions 15, 12, 9, and 5. In some embodiments, the same aliphatic amino acid at each of positions 15, 12, 9, and 5 is a branched chain aliphatic amino acid. In some embodiments, the same aliphatic amino acid at each of positions 15, 12, 9, and 5 is selected from the group consisting of L, I, or V. In some embodiments, the amino acid residue at position 15, 12, 9, and 5 is I. In some embodiments, the amino acid residue at position 15, 12, 9, and 5 is L. In some embodiments, the aliphatic amino acid residue at position 23 is V or L. In some embodiments, the aliphatic amino acid residue at position 23 is V and the aliphatic amino acid residue at position 15, 12, 9, and 5 is I or L. In some embodiments, the aliphatic amino acid at position 23 is V, the aliphatic amino acid at position 19, 4, and 1 is L, and the aliphatic amino acid residue at position 15, 12, 9, and 5 is I or L. In some embodiments, a variant comprises A at positions 14 and 13.

In some embodiments, a peptide of the invention further comprises amino acids at positions 25 and 26, as numbered with reference to any one of SEQ ID NOS:1 to 30, or 31 or 32. In typical embodiments, the amino acid residue at position 25 is K or N and the amino acid residue at position 26 is S, Y, or P. In some embodiments, the amino acid at position 25 is K and the amino acid at position 26 is S.

It will be readily understood by those of skill in the art that the foregoing polypeptides are not fully inclusive of the family of polypeptides of the present invention. In fact, using the teachings provided herein, other suitable polypeptides (e.g., additional conservative variants) can be routinely produced by, for example, conservative or semi-conservative substitutions (e.g., D replaced by E), extensions, deletions and the like. In addition, using the assays provided herein, other suitable polypeptides can be routinely screened for desired biological activities.

Non-identical amino acid residues can be naturally or non-naturally occurring. The term "percent identical" refers to sequence identity between two amino acid sequences (or between two nucleotide sequences, which are also provided by the present invention). Identity can each be determined by comparing a position in each sequence that may be aligned for purposes of comparison. When an equivalent position in the compared sequences is occupied by the same amino acid or base, then the molecules are identical at that position; when the equivalent site is occupied by the same or a similar amino acid residue (e.g., similar in steric and/or electronic nature), then the molecules can be referred to as homologous (similar) at that position. Expression as a percentage of homology, i.e., similarity, or identity refers to a function of the number of similar or identical amino acids at positions shared by the compared sequences. Various alignment algorithms and/or programs can be used, including, for example, FASTA, BLAST and ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid mismatch between the two sequences.

In another exemplary embodiment, which can overlap with the embodiments described above, variants of any one of SEQ ID NOS:1 to 30, are substituted with conservative (or semi-conservative) amino acid residues. The term "conservative amino acid substitutions" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (see, e.g., Schulz, G. E. and R. H. Schirmer, Principles of Protein Structure, Springer-Verlag). According to such analyses, groups of amino acids may be defined where amino acids within a group exchange preferentially with each other and, therefore, resemble each other most in their impact on the overall protein structure (see, e.g., Schulz, G. E. and R. H. Schirmer, Principles of Protein Structure, Springer-Verlag). One example of a set of amino acid groups defined in this manner include: (i) a charged group, consisting of Glu and Asp, Lys, Arg and His; (ii) a positively-charged group, consisting of Lys, Arg and His; (iii) a negatively-charged group, consisting of Glu and Asp; (iv) an aromatic group, consisting of Phe, Tyr and Trp; (v) a nitrogen ring group, consisting of His and Trp; (vi) a large aliphatic nonpolar group, consisting of Val, Leu and Ile; (vii) a slightly-polar group, consisting of Met and Cys; (viii) a small-residue group, consisting of Ser, Thr, Asp, Asn, Gly, Ala, Glu, Gln and Pro; (ix) an aliphatic group consisting of Val, Leu, Ile, Met and Cys; and (x) a small hydroxyl group consisting of Ser and Thr. In the context of this invention, reference to the charge of an amino acid refers to the charge at physiological pH.

In another exemplary embodiment, which again can overlap with the embodiments described above, "a conservative amino acid substitution" can refer to the substitution of an amino acid for another that is similar in molecular weight or similar in hydrophobicity. By "similar molecular weight" and "similar hyrdrophobicity" is meant a value that is within 25%, more preferably 20%, 15%, 10%, or less than 10% of the respective value. Data for amino acid molecular weights and hydrophobicities are set forth in Table 1. A hydrophobicity ranking is set forth in Table 2; a conservative substitution includes exchanging an amino acid that is designated "=" to another (e.g., Tyr=Trp) and exchanging one amino acid for another that is adjacent to it in the ranking order as delineated by the greater and lesser than symbols.

TABLE 1

Parameters for the Unmodified Physiological L-alpha-Amino Acids

| Amino Acid | 3-Letter Code | 1-Letter Code | Molecular Weight† | Hydrophobicity‡ |
|---|---|---|---|---|
| Alanine | Ala | A | 89.09 | 0.616 |
| Cysteine | Cys | C | 121.16 | 0.680 |
| Aspartate | Asp | D | 133.10 | 0.028 |
| Glutamate | Glu | E | 147.13 | 0.043 |
| Phenylalanine | Phe | F | 165.19 | 1.00 |
| Glycine | Gly | G | 75.07 | 0.501 |
| Histidine | His | H | 155.16 | 0.165 |
| Isoleucine | Ile | I | 131.18 | 0.943 |
| Lysine | Lys | K | 146.19 | 0.283 |
| Leucine | Leu | L | 131.18 | 0.943 |
| Methionine | Met | M | 149.21 | 0.738 |
| Asparagine | Asn | N | 132.12 | 0.236 |

TABLE 1-continued

Parameters for the Unmodified Physiological L-alpha-Amino Acids

| Amino Acid | 3-Letter Code | 1-Letter Code | Molecular Weight[†] | Hydrophobicity[‡] |
|---|---|---|---|---|
| Proline | Pro | P | 115.13 | 0.711 |
| Glutamine | Gln | Q | 146.15 | 0.251 |
| Arginine | Arg | R | 174.20 | 0.000 |
| Serine | Ser | S | 105.09 | 0.359 |
| Threonine | The | T | 119.12 | 0.450 |
| Valine | Val | V | 117.15 | 0.825 |
| Tryptophan | Trp | W | 204.23 | 0.878 |
| Tyrosine | Tyr | Y | 181.19 | 0.880 |

[†]The molecular weights given are those of the neutral, free amino acids; residue weights can be obtained by subtraction of one equivalent of water (18 g/mol).
[‡]The hydrophobicities given are the "Scaled" values from computational log(P) determinations by the "Small Fragment Approach" (see, *"Development of Hydrophobicity Parameters to Analyze Proteins Which Bear Post- or Cotranslational Modifications"* Black, S. D. and Mould, D. R., *Anal. Biochem.*, 193: 72-82 (1991)). The equation used to scale raw log(P) values to the scaled values given is as follows: Scaled Parameters = (Raw Parameters + 2.061)/4.484.

TABLE 2

Trend of Hydrophobicity Parameters for the Physiological L-alpha-Amino Acids

Phe > Leu = Ile > Tyr = Trp > Val > Met > Pro > Cys > Ala > Gly > Thr > Ser > Lys > Gln > Asn > His > Glu > Asp > Arg

Another indication that two polypeptides are conservative variants of one another is that the two polypeptides carry out the same function and, in preferred embodiments, the same function at the same or very similar level of activity. Thus, in one embodiment, a conservative variant of a polypeptide of this invention will comprise an activity of at least 80%, 85%, 86%, 87%, 88%, 89%, 90%, 91%, 92%, 93%, 94%, 95%, 96%, 97%, 98%, 99%, or 100% of that found in a polypeptide of SEQ ID NO:31 or 32; and will also not exhibit toxicity when administered at high doses. Again, in some embodiments, the polypeptides of this invention will possess more than one activity. For example, a polypeptide of the invention can comprise cholesterol efflux mediating activity, ABCA stabilization activity, LDL-lowering activity, anti-inflammatory activity as well as antioxidant activity, any combination of these activities or, ideally, all of these activities. Conservative variants can have one or more of the same activities and, ideally, all of the same activities. The screening assays described herein can be readily used by those of skill in the art to determine whether two or more polypeptides possess similar activities. In addition, those of skill in the art will know of other screening assays that can be used to determine whether two or more polypeptides possess similar biological properties or activities.

One of skill understands that amino acid residues may be added to either the C-terminus and/or N-terminus of the polypeptides of the present invention without effecting the activity of such polypeptides. Thus, a polypeptide of the invention that comprises an α-helical sequence as described herein (e.g., any one of SEQ ID NOS:1 to 30), includes embodiments that are over 24 amino acids in length, e.g., peptide that are 25, 26, 28, 30, 32, 35, or 40, or 60 or 100 amino acids in length. One of skill also understands that polypeptides of the invention may also be linked, e.g., via a proline or other linker residues, to another amphipathic α helical peptide that can stimulate cholesterol efflux to form a bi-helix or multimer polypeptide, e.g., of 50, 60, 70, 80, 90, or 100 amino acids in length. Accordingly, a sequence of any of a peptide as described herein can have amino acid additions or can be joined. For example, one molecule of a polypeptide of the invention, e.g., any one of SEQ ID NOS:1 to 30, or variants thereof as described herein, may be joined to another molecule of the polypeptide through a proline residue to provide a polypeptide that is 49 residues in length. Such a polypeptide can have cholesterol efflux activity that exceeds that of a native full-length apolipoproteins (e.g., Apo AI and Apo E), or that of the cholesterol efflux-mediating domain of the apolipoprotein. Using the methodologies described herein, one of skill can readily add additional amino acids to either the C-terminus and/or N-terminus, and then screen the resulting polypeptides for the desired activity.

In some embodiments, a peptide of the invention may be joined to another peptide that has a short half-life to provide a bi-peptide that has a longer half-life than the latter peptide when administered to a subject at a comparable molar dose. In some embodiments, a peptide of the invention may be joined to another physiologically active peptide to provide a dual function hybrid peptide. In some embodiments, a peptide of the invention may be joined to another physiologically active peptide from a cellular protein, or the physiologically active peptide may target a cellular protein, such as a receptor. For example in some embodiments, any one of SEQ ID NOS:1 to 30, or variants thereof as described herein, may be joined to A and B-naturetic peptides (ANP, BNP and variants thereof), which have short half-lifes; bivalidrudin (and other thrombin and Xa inhibitors); or glucose regulating peptides (GLP-1, glucagon and variants of them).

In yet another embodiment, peptidomimetics of the polypeptides of the present invention are provided. A "peptidomimetic" includes any modified form of an amino acid chain, including, but not limited to, phosphorylation, capping, fatty acid modifications and including unnatural backbone and/or side chain structures. It will be readily apparent to those of skill in the art that a peptidomimetic comprises the structural continuum between an amino acid chain and a non-peptide small molecule. Peptidomimetics generally retain a recognizable polypeptide-like polymer unit structure. Thus, a peptidomimetic typically retains the function of binding to any target molecule that a natural polypeptide binds to. Examples of suitable peptidomimetics are disclosed in U.S. Patent Application Publication No. 2006/0069030, the teachings of which are incorporated by reference for all purposes. Other peptidomimetics and methods of making same will be known to those of skill in the art.

Peptidomimetics of the present invention fall into one of two categories: (i) surrogates; and (ii) analogs. Numerous surrogates have been developed for the amide bond of polypeptides. Frequently exploited surrogates for the amide bond include, but are not limited to, the following groups: (i) trans-olefins, (ii) fluoroalkene, (iii) methyleneamino, (iv) phosphonamides, and (v) sulfonamides. Additionally, peptidomimetics based on more substantial modifications of the backbone of a polypeptide can be used. Peptidomimetics that fall in this category include (i) retro-inverso analogs, and (ii) N-alkyl glycine analogs (so-called peptoids). Examples of surrogates and analogs are disclosed in U.S. Patent Application Publication No. 2006/0069030.

In another embodiment, the peptide or peptidomimetic may comprise D amino acids, or analogs thereof, or a mixture of D and L amino acids. Such peptides can be synthesized from commercially using standard solid- or solution-phase polypeptide-synthesis techniques.

In still another embodiment, the peptidomimetic is a trans-olefin surrogate peptide or derivative. Such trans-olefin peptides can be readily synthesized according to the method of Shue et al., *Tetrahedron Lett.*, 28:3225 (1987). In addition, other methods known in the art can also be used. It will be appreciated that variations in the procedure of Sjue et al., or other procedures available, may be necessary depending on the nature of the reagents used in synthesizing the trans-olefin derivative.

It is also possible to couple the pseudodipeptides synthesized by the above method to other pseudodipeptides, to make pseudopeptides with several olefinic functionalities in place of amide functionalities. For example, pseudodipeptides corresponding to certain di-peptide sequences can be made and then coupled together by standard techniques to yield an analog of the polypeptide that has alternating olefinic bonds between residues.

Still another class of peptidomimetic derivatives includes phosphonate derivatives. The synthesis of such phosphonate derivatives can be adapted from known synthesis schemes (see, for example, Loots et al. in "Peptides: Chemistry and Biology," (Escom Science Publishers, Leiden, p. 118, 1988); Petrillo et al. in "Peptides: Structure and Function (Proceedings of the 9th American Peptide Symposium)," (Pierce Chemical Co. Rockland, Ill., 1985).

In other embodiments, a polypeptide of the invention can be modified. One example of a modification is the introduction of carbohydrate or lipid moieties. Such modifications can change the solubility of the polypeptides in various mediums so that they can advantageously be prepared as a suitable pharmaceutical composition. Modifying lipid groups include, but are not limited to, farnesyl groups and myristoyl groups. Modifying carbohydrate groups include, but are not limited to, single sugars or oligosaccharides of any naturally occurring and/or synthetic sugar and sugar alcohols including, for example, glucose, galactose, rhamnose, mannose, arabinose, and other sugars, and their respective alcohols.

In certain embodiments, a polypeptide of the invention may further comprise modifications analogous to post-translational modifications. Such modifications include, but are not limited to, acetylation, carboxylation, glycosylation, phosphorylation, lipidation, and acylation. As a result, the modified peptidomimetics may contain non-amino acid elements, such as polyethylene glycols, lipids, poly- or monosaccharide, and phosphates. Effects of such non-amino acid elements on the functionality of a peptidomimetic can be tested using the assay methods disclosed herein.

In particular embodiments, the peptidomimetics include at least one backbone linkage that is not an amide linkage in the amino to carboxy direction.

As previously described, reference to an "amino acid" in the present context refers to both naturally occurring and unnaturally occurring amino acids. Accordingly, a peptide of present invention may comprise one or more amino acid analogs. Examples of amino acid analogs, include, but are not limited to, the following:

an alkyl, aryl, acyl, azido, cyano, halo, hydrazine, hydrazide, hydroxyl, alkenyl, alkynyl, ether, thiol, sulfonyl, sulfo, seleno, ester, thioacid, borate, boronate, phospho, phosphono, heterocyclic, enone, imine, aldehyde, alkoxyamine, hydroxylamine, keto, or amino substituted amino acid, or any combination thereof; a glycosylated or carbohydrate modified amino acid; a keto containing amino acid; a sugar substituted amino acid, e.g., a sugar substituted serine or the like; a carbon-linked sugar-containing amino acid; a sugar-substituted cysteine; a redox-active amino acid; an α-hydroxy containing acid; an amino thio acid containing amino acid; an α,α disubstituted amino acid; a β-amino acid; sulfotyrosine, 4-borono-phenylalanine, an aminooxy amino acid, an aminooxy lysine, an aminooxy ornithine, an aminooxy tyrosine, or a cyclic amino acid other than proline. Other unnatural amino acids include, but are not limited to, unnatural amino acids comprising any one or more of the following functional groups: an aldehyde moiety, a keto moiety, a beta-diketo moiety, an alkoxyamine moiety, an acyl hydrazide moiety, a dehydroalanine moiety, a thioester moiety, an ester moiety, a boronate moiety, an azide moiety, an acetylenic moiety, an olefinic moiety, a vicinal thiol amine moiety, and the like. Unnatural amino acids include, N-substituted glycines, N-methyl amino acids, phenylalanine analogs, and derivatives of lysine (Lys), ornithine (Orn) and α,γ-diaminobutyric acid (Dbu) in either the L- or D-configuration that function in a manner similar to the naturally-occurring amino acids.

Additional examples of unnatural amino acids include, but are not limited to, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiarybutylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid, thioproline, aminophenylalanine, hydroxytyrosine, and aminotyrosine. In some other embodiments, an unnatural amino acid may be 1-aminocyclopentane-1-carboxylic acid (Acp), 1-aminocyclobutane-1-carboxylic acid (Acb), 1-aminocyclopropane-1-carboxylic acid (Acpc), homocitrulline (HoCit), α-aminohexanedioic acid (Aad), 3-(4-pyridyl)alanine (4-Pal), 3-(3-pyridyl)alanine (3-Pal), propargylglycine (Pra), α-aminoisobutyric acid (Aib), α-aminobutyric acid (Abu), norvaline (Nva), α,β-diaminopropionic acid (Dpr), α,γ-diaminobutyric acid (Dbu), α-tert-butylglycine (Bug), 3,5-dinitrotyrosine Tyr(3, 5-di $NO_2$), norleucine (Nle), 3-(2-naphthyl)alanine (Nal-2), 3-(1-naphthyl)alanine (Nal-1), cyclohexylalanine (Cha), di-n-propylglycine (Dpg), cyclopropylalanine (Cpa), homoleucine (Hle), homoserine (HoSer), homoarginine (Har), homocysteine (Hcy), methionine sulfoxide (Met(O)), methionine methylsulfonium (Met (S-Me)), α-cyclohexylglycine (Chg), 3-benzo-thienylalanine (Bta), taurine (Tau), hydroxyproline (Hyp), O-benzyl-hydroxyproline (Hyp(Bzl)), homoproline (HoPro), β-homoproline ((βHoPro), thiazolidine-4-carboxylic acid (Thz), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 5H-thiazolo [3,2-a]pyridine-3-carboxylic acid (Btd), 3-aminobenzoic acid (3-Abz), 3-(2-thienyl)alanine (2-Thi), 3-(3-thienyl)alanine (3-Thi), α-aminooctanedioc acid (Asu), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-$NO_2$)), 1-amino-1-cyclohexane carboxylic acid (Ach), 1-amino-1-(3-piperidinyl)carboxylic acid (3-Apc), 1-amino-1-(4-piperidinyl)carboxylic acid (4-Apc), 2-amino-3-(4-piperidinyl) propionic acid (4-App), 2-aminoindane-2-carboxylic acid (Aic), 2-amino-2-naphthylacetic acid (Ana), (2S, 5R)-5-phenylpyrrolidine-2-carboxylic acid (Ppca), 4-thiazoylalanine (Tha), 2-aminooctanoic acid (Aoa), 2-aminoheptanoic acid (Aha), ornithine (Orn), azetidine-2- carboxylic acid (Aca), α-amino-3-chloro-4,5-dihydro-5-isoazoleacetic acid (Acdi), thiazolidine-2-carboxylic acid (Thz(2-COOH)), allylglycine (Agl), 4-cyano-2-aminobutyric acid (Cab), 2-pyridylalanine (2-Pal), 2-quinoylalanine (2-Qa1), cyclobutylalanine (Cba), a phenylalanine analog, a lysine derivative, a ornithine (Orn) derivative, an α,γ-diaminobutyric acid Dbu derivative, stereoisomers thereof, and combinations thereof (see, Liu and Lam, *Anal. Biochem.*, 295:9-16 (2001)). As such, the unnatural α-amino acids are present either as unnatural L-α-amino acids, unnatural D-α-amino acids, or combinations thereof. Additional suitable amino acid analogs include, without limitation, β-amino acids and γ-amino acids. Suitable R groups for β- or γ-amino acids include, but are not limited to, side-chains present in naturally-occurring amino acids and unnatural amino acids. N-methyl amino acids include N-methyl-Ala, N-methyl-Cys, N-methyl-Asp, N-methyl-Glu, N-methyl-Phe, N-methyl-Gly, N-methyl-His, N-methyl-Ile, N-methyl-Arg, N-methyl-Lys, N-methyl-Leu, N-methyl-Met, N-methyl-Asn, N-methyl-Gln, N-methyl-Ser, N-methyl-Thr, N-methyl-Val, N-methyl-Trp, N-methyl-Tyr, N-methyl-Acp, N-methyl-Acb, N-methyl-Acpc, N-methyl-Cit, N-methyl-HoCit, N-methyl-Aad, N-methyl-4-Pal, N-methyl-3-Pal, N-methyl-Pra, N-methyl-Aib, N-methyl-Abu, N-methyl-Nva, N-methyl-Dpr, N-methyl-Dbu, N-methyl-Nle, N-methyl-Nal-2, N-methyl-Nal-1, N-methyl-Cha, N-methyl-Cpa, N-methyl-Hle, N-methyl-HoSer, N-methyl-Har, N-methyl-Hcy, N-methyl-Chg, N-methyl-Bta, N-methyl-2-Thi, N-methyl-3-Thi, N-methyl-Asu, N-methyl-Acdt, N-methyl-Ahch, N-methyl-Akch, N-methyl-Actp, N-methyl-Tyr(3-$NO_2$), N-methyl-Ach, N-methyl-3-Apc, N-methyl-4-Apc, N-methyl-4-App, N-methyl-Tha, N-methyl-Aoa, N-methyl-Aha, N-methyl-Orn, N-methyl-Aca, N-methyl-Agl, N-methyl-Cab, N-methyl-2-Pal, N-methyl-Cba, N-methyl-HoPhe, N-methyl-Phg, N-methyl-Phe(4-$NH_2$), N-methyl-4-Phe(4-Me), N-methyl-Phe(4-F), N-methyl-Phe(4-C1), N-methyl-Phe(2-Br), N-methyl-Phe(3-Br), N-methyl-Phe(4-Br), N-methyl-Phe(3-$CF_3$), N-methyl-Phe(4-$CF_3$), N-methyl-Phe(4-$NO_2$), N-methyl-Phe(4-CN), N-methyl-Bpa, N-methyl-Phg(4-C1), N-methyl-Phg(4-Br), N-methyl-Tyr (Me), N-methyl-Lys38, N-methyl-Lys27, N-methyl-Lys73, N-methyl-Lys55, N-methyl-Lys28, N-methyl-Lys72, N-methyl-Lys12, N-methyl-Lys123, N-methyl-Lys63, N-methyl-Lys124, N-methyl-Lys82, N-methyl-Lys31, N-methyl-Lys15, N-methyl-Lys125, N-methyl-Lys43, N-methyl-Lys24, N-methyl-Lys5, N-methyl-Lys4, N-methyl-Lys50, N-methyl-Lys81, N-methyl-Orn38, N-methyl-Orn27, N-methyl-Orn73, N-methyl-Orn55, N-methyl-Orn28, N-methyl-Orn72, N-methyl-Orn12, N-methyl-Orn123, N-methyl-Orn63, N-methyl-Orn124, N-methyl-Orn82, N-methyl-Orn31, N-methyl-Orn15, N-methyl-Orn125, N-methyl-Orn43, N-methyl-Orn24, N-methyl-Orn5, N-methyl-Orn4, N-methyl-Orn50, N-methyl-Orn81, N-methyl-Dbu38, N-methyl-Dbu27, N-methyl-Dbu73, N-methyl-Dbu55, N-methyl-Dbu28, N-methyl-Dbu72, N-methyl-Dbu12, N-methyl-Dbu123, N-methyl-Dbu63, N-methyl-Dbu124, N-methyl-Dbu82, N-methyl-Dbu31, N-methyl-Dbu15, N-methyl-Dbu125, N-methyl-Dbu43, N-methyl-Dbu24, N-methyl-Dbu5, N-methyl-Dbu4, N-methyl-Dbu50, N-methyl-Dbu81, stereoisomers thereof, and combinations thereof.

Analogs of lysine (Lys), ornithine (Orn) and α,γ-diaminobutyric acid (Dbu) include, without limitation, Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Orn81, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81, stereoisomers thereof, and combinations thereof. Derivatives of Orn and Dbu are similar to the lysine derivatives with corresponding carboxylic acid attached to the side chain of Orn and Dbu, respectively. Hydrophobic amino acid analogs of leucine, valine, isoleucine, glycine, alanine, methionine include norvaline (Nva), 1-aminocyclopropane-1-carboxylic acid (Acpc), 1-aminocyclobutane-1-carboxylic acid (Acb), α-cyclohexylglycine (Chg), α-aminoisobutyric acid (Aib), α-aminobutyric acid (Abu), 3-(2-thienyl)alanine (2-Thi), 3-(3-thienyl)alanine (3-Thi), 3-(3-pyridyl)alanine (3-Pal), 3-(2-naphthyl)alanine (Nal-2), 2-amino-2-naphthylacetic acid (Ana), 3,5-dinitrotyrosine (Tyr(3,5-di $NO_2$)), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-$NO_2$)), 1-amino-1-cyclohexane carboxylic acid (Ach), 2-aminoindane-2-carboxylic acid (Aic), (2S,5R)-5-phenylpyrrolidine-2-carboxylic acid (Ppca), 4-thiazoylalanine (Tha), 2-aminooctanoic acid (Aoa), 2-aminoheptanoic acid (Aha), and a stereoisomer thereof. Preferably, the proline analog is hydroxyproline.

Analogs of negatively charged amino acids include α-aminohexanedioic acid, α-aminooctanedioc acid, homoaspartic acid, γ-carboxy-glutamic acid, 4-carboxyphenylalanine, and a stereoisomer thereof. In other embodiments, the negatively charged amino acid is selected from Aad, Bec and Bmc.

Protecting Groups

The polypeptides as well as the peptidomimetics of the present invention, including, for example, the retro-inverso peptidomimetics, can be modified so that the R-groups on the constituent amino acids and/or the terminal amino acids are blocked, i.e., protected, by a protecting group. As used herein, "protecting group" refers to a temporary substituent that protects a potentially reactive functional group from undesired chemical transformations.

Examples of such protecting groups generally include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, $2^{nd}$ ed.; Wiley: New York, 1991).

A wide number of protecting groups are suitable for this purpose. Such groups include, but are not limited to, acetyl, $CH_3$—$(CH_2)_n$—CO—, amide, Fmoc, t-butoxycarbonyl (t-BOC), 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (Bzl), Benzyl (Bzl), Benzoyl (Bz), 3-nitro-2-pyridinesulphenyl (Npys), 1-(4,4-dimethyl-2,6-dioxocyclohexylidene) ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), cyclohexyloxy (cHxO), t-butoxymethyl (Bum), t-butoxy (tBuO), t-Butyl (tBu), and Trifluoroacetyl (TFA). The variable "n" is an integer from 0 to 12, typically 0 to 6 such as 0 to 4. Other suitable protecting groups are disclosed in U.S. Pat. No. 6,933,279, the teachings of which are incorporated by reference.

In one embodiment, preferred protecting groups include, but are not limited to, acetyl, amide, and alkyl groups with acetyl and alkyl groups being particularly preferred for N-terminal protection and amide groups being particularly preferred for carboxyl terminal protection. In one preferred embodiment, an acetyl group is used to protect the amino terminus and an amide group is used to protect the carboxyl terminus. In this embodiment, acetylation can be accomplished during the synthesis when the polypeptide is on the resin using acetic anhydride. Amide protection can be achieved by the selection of a proper resin for the synthesis. For instance, a rink amide resin can be used. After the completion of the synthesis, the semipermanent protecting groups on acidic bifunctional amino acids, such as Asp and Glu, and basic amino acids, such as Lys, as well as the hydroxyl of Tyr, are all simultaneously removed. The polypeptides released from such a resin using acidic treatment comes out with the N-terminal protected as acetyl and the C-terminal protected as $NH_2$, with the simultaneous removal of all of the other protecting groups.

In one embodiment, the polypeptides of the present invention comprise one or more D-amino acids as described herein. In certain embodiments, every amino acid (e.g., every enantiomeric amino acid) is a D-amino acid. D-amino acids are readily incorporated at one or more positions in the polypeptide using a D-form derivatized amino acid residue in the chemical synthesis. D-form residues for solid phase polypeptide synthesis are commercially available from a number of suppliers (see, e.g., Advanced Chem Tech, Louisville, Ky.; Nova Biochem, San Diego, Calif.; Sigma, St Louis, Mo.; Bachem California Inc., Torrance, Calif., etc.). The D-form amino acids can be incorporated at any position in the polypeptide as desired. Thus, for example, in one embodiment, the polypeptide can comprise a single D-amino acid, while in other embodiments, the polypeptide comprises at least two, generally at least three, more generally at least four, most generally at least five, preferably at least six, more preferably at least seven and most preferably at least eight D amino acids. In one embodiment, essentially every other (enantiomeric) amino acid is a D-form amino acid. In certain embodiments, at least 80%, preferably at least 90%, more preferably at least 95% of the enantiomeric amino acids are D-form amino acids. In one particularly preferred embodiment, essentially every enantiomeric amino acid is a D-form amino acid.

While in preferred embodiments, the polypeptides of this invention utilize naturally-occurring amino acids or D forms of naturally occurring amino acids, substitutions with non-naturally occurring amino acids (e.g., methionine sulfoxide, methionine methylsulfonium, norleucine, episilon-aminocaproic acid, 4-aminobutanoic acid, tetrahydroisoquinoline-3-carboxylic acid, 8-aminocaprylic acid, 4-aminobutyric acid, Lys(N(epsilon)-trifluoroacetyl), α-aminoisobutyric acid, and the like) can be used in the polypeptides of the present invention. As with the other amino acid substitutions, non-naturally occurring amino acids are typically substituted so that, upon substitution, they retain the spatial and ionic or non-ionic character of the residue that they substitute.

In some embodiments, a citrulline is replaced with a citrulline analog amino acid. Such analogs and their preparation are known to the person skilled in the art. See, for example, Sonke, et al., in Stereoselective Biocatalysis (2000), pp. 23-58, and Greene: Protective Groups in Organic Synthesis (Wiley, New York 1999). Example of citrulline amino acid analogs can be found in U.S. Pat. No. 7,888,133.

In some embodiments, non-naturally occurring amino acids are employed at positions in the peptide where non-naturally occurring amino acids have long, e.g., $C_{5-8}$, carbon alkenyl or alkanyl side chains.

In some embodiments, a variant of any one of SEQ ID NOS:1 to 30 may comprise a chemical staple. For example, α-methylated amino acids containing olefinic side chains of varying length are introduced at the (i) and (i+7) positions of the peptide sequence and then cyclized by olefin metathesis. As used herein, (i) refers to a reference amino acid residue and the term (i+x) refers to an amino acid x residues from the (i) amino acid. By making the peptides more resistant to degradation and enabling their cellular uptake, the hydrocarbon staple overcomes some of the classic shortcomings of peptide therapeutics. Stapled peptides retain their natural shape, are resistant to degradation, and can enter and exert their intended function in cells. Stapled peptides are known in the art. (See, for example, Verdine and Helinski Methods Enzymol. 2012; 503:3-3; Schafineister et al. J Am Chem Soc 122:5891-92 (2000)). See, also U.S. Patent Publication No. US2005/0250680, which is herein incorporated by reference in its entirety. In the present invention, it is understood that when a chemical staple is said to be present at a particular residue, e.g., at a position 3, 14, or 23 of SEQ IDNO:31 or at a position 22, 11, or 2 SEQ ID NO:2, or variants thereof, there is a corresponding residue in the peptide e.g. at a position that is four or seven residues from the recited position that is also a stapling residue such that a staple linkage is formed.

Preparation of Peptides

Polypeptides of the invention can be prepared using known techniques. For example, peptides can be chemically synthesized, e.g., solid phase synthesis; or can be expressed recombinantly, especially when the polypeptide comprises naturally occurring amino acid residues. One of skill can generate a nucleic acid encoding a polypeptide of the invention and obtain high level expression using standard techniques. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009, supplements through 2013).

Methods of Identifying Polypeptides with Desired Activity

The polypeptides or peptidomimetics of the present invention can be readily evaluated for their ability to mediate cholesterol efflux and/or stabilize ABCA (e.g., ABCA1) using methods well known to those of skill in the art. Peptides may be additionally evaluated for toxicity.

A number of different screening protocols can be utilized to identify polypeptides or peptidomimetics of the present invention that mediate cholesterol efflux and/or stabilize ABCA (e.g., ABCA1). In one embodiment, the screening methods involve screening a plurality of test polypeptides to identify those polypeptides that mediates cholesterol efflux and/or stabilizes ABCA (e.g., ABCA1) in, e.g., mammalian cells, including human cells.

In addition to screening for their ability to mediate cholesterol efflux and/or stabilize ABCA, candidate test polypeptides can also be screened for other activities including, e.g., anti-oxidant activities and anti-inflammatory activities. A number of different screening protocols can be utilized to identify polypeptides or peptidomimetics of the present invention that have anti-oxidant activity and/or anti-inflammatory activity.

It will be readily apparent to those of skill in the art that numerous other screening assays, in addition to those disclosed herein, can be used to screen the polypeptides or peptidomimetics of the present invention for the desired biological activites.

Activity Assays—Cholesterol Efflux Activity

Suitable cholesterol efflux assays are described in, e.g., Bielicki, J. K and Oda, M. N., *Biochemistry*, 41:2089-2096 (2002); Jia et al., *Biochem. Biophys. Res. Common.*, 297: 206-213 (2002). In some embodiments, a polypeptide known to mediate cholesterol efflux (e.g., helix 9/10 of Apo A-I) is used to screen for additional mediators of cholesterol efflux in a cell based assay. For example, cell lines in which cholesterol efflux can be enhanced using a cAMP analog that up-regulates ABCA1 protein expression (e.g., J774 macrophages) can conveniently be used to assess the ability of a polypeptide of the present invention to mediate cholesterol efflux. The cells are incubated with labeled cholesterol (e.g., [$^3$H]cholesterol) under conditions appropriate for cholesterol uptake by the cells. Thus, cAMP or cAMP analogs (e.g., CPT-cAMP) are incubated with the cells for a suitable time before the initiation of cellular cholesterol efflux, i.e., prior to contacting the cells with a test polypeptide. Measurement of labeled cholesterol appearing in the medium is used to determine the cholesterol efflux mediating activity of the test polypeptide.

Activity Assays—ABCA Stabilization Activity

Multiple assays known in the art can be used to measure the ABCA stabilization activity of a polypeptide of the invention. For example, binding assays can be used to test the ability of the test polypeptide to bind to ABCA (e.g., ABCA1). It has been found that polypeptides having ABCA stabilization activity are also likely mediators of cholesterol efflux. As such, in a preferred embodiment, the polypeptides or peptidomimetics of the present invention have the ability to mediate cholesterol efflux and to stabilize ABCA. In one screening embodiment, the binding assays can be competitive assays. Other assays include, for example, direct measurement of ABCA (e.g., ABCA protein or nucleic acids) following contact with the test polypeptide.

Binding Assays

Binding assays usually involve contacting ABCA with one or more test polypeptides, and allowing sufficient time for ABCA and the test polypeptides to form a binding complex. Any binding complexes formed can be detected using any of a number of established analytical techniques. Protein binding assays include, but are not limited to, immunohistochemical binding assays, flow cytometry or other assays. In some embodiments, competition assays are used to determine whether a test polypeptide has ABCA stabilization activity. Competition assays are well known in the art. Typically, a competitor compound, i.e., a compound known to bind ABCA, is labeled so that differences in binding to ABCA (e.g., in the presence of increasing amount of a test polypeptide of the invention that may bind to ABCA) can be measured. The particular label or detectable group used in the assay is not a critical aspect of the invention, as long as it does not significantly interfere with the binding of the test compound to ABCA.

In some embodiments, ABCA expressing and non-expressing cells are used to measure the ABCA (e.g., ABCA1) stabilization activity of a test polypeptide by measuring the relative ABCA binding affinities of the test polypeptide and a competitor compound (e.g., full-length Apo A-I A or Apo A-I 9/10 polypeptide) for ABCA. In some embodiments, the binding affinity of full-length Apo A-I A to ABCA is compared to the binding affinity of a labeled polypeptide of the invention as described in, e.g., Remaley et al., *J. Lipid Res.*, 44:828-836 (2003). Cells expressing ABCA are incubated in the presence and absence of the competitor compound, and then exposed to a range of concentrations of individual labeled test polypeptides (e.g., a radiolabeled polypeptide of the invention). Typically, the concentrations of test polypeptides will range from about 0.1 µg/ml to about 200 µg/ml, about 0.5 µg/ml to about 100 µg/ml, about 1 µg/ml to about 40 µg/ml, or about 5 µg/ml to about 20 µg/ml.

Direct Measurement of ABCA

In some embodiments, the stabilization of ABCA is measured by direct measurement of ABCA (e.g., ABCA protein, or nucleic acid) using a cell based assay. Cell based assays can be performed in any cells in which ABCA is expressed (e.g., J774 macrophages), including cells which have been transfected with ABCA (e.g. HeLa cells). Any cell type can be used. For example, J774 macrophages can be used to assess relative ABCA1 protein levels in the presence and absence of polypeptides of the invention. The cells are first contacted with a compound that will induce ABCA (e.g., cAMP or a cAMP analogue such as, 8-bromo-cAMP) to upregulate ABCA (e.g., ABCA1) expression, then exposed to synthetic ABCA1 protein levels in the presence and absence of polypeptides of the invention in the absence of the cAMP stimulus to evaluate whether ABCA1 protein was stabilized or degraded. Relative levels of ABCA1 protein can be assessed using any means known in the art including, e.g., immunoblot analysis of cell membranes (Oram et al., *J. Biol. Chem.*, 278:52379-52385 (2003)) or hybridization of nucleic acid probes to ABCA mRNA.

Toxicity Assays

Peptides or peptidomeimetics of the invention can be evaluated for toxicity using known assays. Examples of such assays are illustrated in the Examples section. Toxicity is typically assayed in a rat, rabbit, mouse, monkey or dog model. In an illustrative assay such as that described in Example 1, a peptide is administered intravenously using a rabbit or rat model at doses of 3, 30, and 300 mg/kg and vehicle alone is also administered at 48 hour intervals for a total of four injections. Safety chemistry panels including plasma alanine aminotransferase (ALT), aspartate amino transferase (AST), and creatine kinase (CK) can then be determined in the blood. The presence of elevated levels of these enzymes in the blood compared to control normal values is indicative of toxicity. A peptide of the invention is typically considered to be non-toxic or to have little toxicity, when the results using the highest dose, 300 mg/kg in this illustrative assay, are equivalent (fall within the standard deviation) of the values measured for the control animals that received vehicle alone, or are no more than 2 or 3 times background obtained with vehicle alone. In some embodiments, a toxicity assay is performed where the toxicity of a peptide of the invention is compared to that to ATI-5261 (which has a sequence EVRSKLEEWFAAFRE-FAEEFLARLKS; SEQ ID NO:33). A peptide of the invention that has no or little toxicity typically exhibits less than 50%, preferably less than 20%, or more preferably less than 10% of the toxicity observed with ATI-5261 when administered to a mouse, rat or rabbit at a dose of 300 mg/kg, e.g., 4 hours after injection. Other animal models, e.g., monkeys, may also be used to evaluate toxicity.

Further Testing

Polypeptides that are initially identified as mediating cholesterol efflux or interacting with ABCA can be further tested to validate their ability to mediate cholesterol efflux and/or stabilize ABCA. The basic format of such methods involves administering a lead compound identified during an initial screen to an animal that serves as a model. The animal models utilized in validation studies generally are mammals of any kind. Specific examples of suitable animals include, but are not limited to, primates (e.g., chimpanzees, monkeys, and the like) and rodents (e.g., mice, rats, guinea pigs, rabbits, and the like). In a preferred embodiment, Apo E−/− mice, Apo A-II−/− mice, or Apo C-III−/− mice are used. Additional animal models are described in, e.g., Marschang et al., Sem. Cell Dev. Biol., 14:25-35 (2003).

Peptides may additionally be screened for the ability to lower glucose using known methods. For example, the ability to lower glucose can be evaluated using animal models, such as mice or rats. Mice, e.g., C57Bl/6 mice, fed a normal lab chow diet are injected IP with a peptide that is undergoing evaluation, e.g., at a does of 300 mg/kg, and the glucose levels in the blood are measured at a time period, e.g. 6 hours, following injection and compared to the levels of blood glucose in a control animal that received PBS. Peptides that have glucose lowering activity show statistically significant lowered glucose relative to controls. Typically, peptides lower glucose by at least 5%, often at least 10% or greater, relative to controls. Peptides may also be evaluated for glucose-lowering activity in animal models of obesity, e.g., DIO mice. Further, peptides may be evaluated for the ability to improve sensitivity to insulin using known methods.

Additionally, peptides may be screened for the ability to treat a symptom of Alzheimer's Disease using known methods, including methods comprising evaluating general or selective effects on apoE4 and apoE3 allele-associated Alzheimer's disease in known models. For example, levels of P-tau and/or amyloidβ42 in the brain of human apoE3 or apoE4 replacement mice that express human apoE3 or apoE4 are evaluated. Peptides that have the ability to treat a symptom of Alzheimer's Disease show statistically significant lowered P-tau and/or amyloidβ42 levels relative to controls.

Peptides may be screened for activity using any format. For example, high throughput screening methods may be used to identify polypeptides or peptidomimetics of the present invention that mediate cholesterol efflux and/or stabilize ABCA.

Pharmacokinetics and Cell Targeting

The peptides bind to HDL and assume the long HDL half-life, estimated to be 8 hours in rats and 3-5 days in humans, thereby allowing administration with long intervals. The peptides when bound to other peptides, small molecules or moieties (the cargo molecules) can in an analogous manner increase the half-life of these molecules. The HDL binding properties in plasma and the ABCA1 cell binding of the peptide creates unique PK, tissue and cell distribution properties of the peptide and its cargo that can be used for diagnostic and therapeutic purposes, including but not limited to heart failure, vascular disease, diabetes mellitus, cancer and neurological diseases.

Methods of Use

The non-naturally occurring polypeptides of the present invention use the potent Reverse Cholesterol Transport (RCT) pathway to mediate cholesterol efflux. In addition to being potent and selective mediators of ABCA1-dependent cholesterol efflux, the polypeptides of the present invention also have ABCA stabilization activity, anti-diabetic activity, anti-oxidant activity as well as anti-inflammatory activity, any combination of these activities and, preferably, all of these activities.

In view of their biological activities and, in particular, their ability to mediate cholesterol efflux, the polypeptides of the present invention (or peptidomimetics thereof) can be used to treat elevated cholesterol levels in a mammal, or to treat prophylactically a mammal at risk of developing elevated cholesterol levels. In addition, the polypeptides or peptidomimetics can also be used for improving the lipid parameters in a mammal. An improvement in "lipid parameters" includes, for example, one or more of a decrease in the propensity of lipoproteins to adhere to a blood vessel, a decrease in the amount of atherosclerotic plaque (even though plasma LDL and/or HDL concentrations may not significantly changed), a reduction in the oxidative potential of an HDL or LDL particle, a regression in atherosclerosis (e.g., as measured by carotid angiography or ultrasound) and a reduction in cardiac events. Thus, the polypeptides or peptidomimetics of the present invention can be used to treat or prevent (i.e., prophylactically treat) diseases and conditions associated with dyslipidemia, hypercholesterolemia and inflammation, diabetes, or diseases and conditions that are treatable by altering lipid parameters, such as those diseases and conditions disclosed herein. In some embodiments, the peptides can be used to treat a patient that has a complication of a disease as described herein. Thus, in some embodiments, the patient has macro or microvascular disease, chronic kidney disease, or congestive heart failure.

In addition to the diseases and conditions specifically disclosed herein, those of skill in the art will know of other diseases and conditions associated with dyslipidemia, hypercholesterolemia and inflammation that can be treated or prevented using the polypeptides or peptidomimetics of the present invention.

Treating or Preventing a Symptom(s) of Atherosclerosis

In one embodiment, the present invention provides methods for treating, ameliorating and/or preventing one or more symptoms of atherosclerosis. The methods preferably involve administering to an organism, preferably a mammal and, more preferably, a human, one or more of the polypeptides of this invention (or peptidomimetics of such polypeptides). The polypeptide(s) can be administered, as described herein, according to any of a number of standard methods including, but not limited to, injection, suppository, nasal spray, time-release implant, transdermal patch, orally and the like. In one particularly preferred embodiment, the polypeptide(s) is administered orally (e.g., as a syrup, capsule, tablet, etc.).

The methods of the present invention are not limited to treating humans or non-human animals having one or more symptom(s) of atherosclerosis (e.g., hypertension, narrowing of vessels, plaque formation and rupture, heart attack, angina, or stroke, high levels of plasma cholesterol, high levels of low density lipoprotein, high levels of very low density lipoprotein, or inflammatory proteins, etc.), but are also very useful in a prophylactic context. Thus, the polypeptides of this invention (or peptidomimetics thereof) can be administered to an organism, such as a human or non-human animal, to prevent the onset, i.e., development, of one or more symptoms of atherosclerosis. Suitable candidate subjects for prophylactic treatment include, for example, those subjects having one or more risk factors for atherosclerosis (e.g., family history, genetic markers that correlate with atherosclerosis, hypertension, obesity, high alcohol consumption, smoking, high blood cholesterol, high blood triglycerides, elevated blood LDL, VLDL, IDL, or low HDL, diabetes, or a family history of diabetes, high blood lipids, heart attack, angina or stroke, etc.).

Treatment can complement or obviate the need for invasive procedures and vascular surgery making anti-atherosclerosis treatment systemic and sustainable. Thus, the peptide can be given before intervention to optimize circulation before surgery, during surgery for regional administration in the vasculature or its vicinity, or post-surgery to lessen inflammation and atherosclerosis caused by mechanical trauma by surgical intervention.

Treating or Preventing a Symptom(s) of Atherosclerosis Associated with an Acute Inflammatory Response The atherosclerosis-inhibiting polypeptides of this invention are also useful in a number of other contexts. In particular, it has been found that cardiovascular complications (e.g., atherosclerosis, stroke, etc.) frequently accompany or follow the onset of an acute phase inflammatory response. Such an acute phase inflammatory response is often associated with a recurrent inflammatory disease (e.g., leprosy, tuberculosis, systemic lupus erythematosus, rheumatoid arthritis, etc.), a viral infection (e.g., influenza, HIV, etc.), a bacterial infection, a fungal infection, an organ transplant, a wound or other trauma, an implanted prosthesis, a biofilm, and the like.

In view of their antioxidant activity, the polypeptides described herein can be used to reduce or prevent the formation of oxidized phospholipids during or following an acute phase inflammatory response, thereby mitigating or eliminating cardiovascular complications associated with such a condition. The inflammatory response can also be of more chronic nature as in alcoholic and non-alcoholic liver disease, chronic kidney disease and congestive heart failure.

Treating or Preventing a Disorder Involving Abnormal Glucose Metabolism

In a further aspect, the invention provides a method of altering mammal that has abnormal glucose metabolism. In some embodiment, the mammal has Type II diabetes. In some embodiments, the mammal has Type I diabetes. In some embodiment, the mammal has pre-diabetes or metabolic syndrome. In some embodiments, the mammal is a human. I some embodiments, the mammal is a human that has a fasting blood glucose level of over 100 mg/dL. In some embodiments the mammal has complications of diabetes as macro or microvascular disease, kidney disease or congestive heart failure.

Treating or Preventing Alzheimer's Disease or Mild Cognitive Impairment

In a further aspect, the invention provides a method of treating a human patient that has Alzheimer's Disease or Mild Cognitive Impairment, frontotemporal dementia; or vascular dementia.

As used herein, "Alzheimer's disease" refers to senile dementia as diagnosed using commonly accepted criteria in the art, such as the criteria set forth by The National Institute of Neurological and Communicative Disorders and Stroke and the Alzheimer's disease and Related Disorders Association and/or the criteria as listed in the Diagnostic and Statistical Manual of Mental Disorders (DSM-IV-TR) published by the American Psychiatric Association. The Diagnostic and Statistical Manual of Mental Disorders (Fourth Edition, revised in 2000), also known as the DSM-IV-TR, outlines a detailed set of criteria for the diagnosis of Alzheimer's disease.

In some embodiments, a patient may have mild to moderate dementia, or early-stage Alzheimer's disease, which can be identified using neurological testing and other clinical endpoints. For example, a subject with mild to moderate dementia, e.g., Alzheimer's disease, can be identified using the Mini-Mental State Examination (MMSE). Typically, a score of 16 to 26 (both inclusive) is indicative of mild to moderate Alzheimer's disease. Patients with advanced Alzheimer's disease can also be identified based on clinical parameters. Subjects with this form of Alzheimer's disease may no longer respond to therapy with acetylcholinesterase inhibitors, and may have a markedly reduced acetylcholine level.

In some embodiments, a patient treated with a peptide of the invention may have Mild Cognitive Impairment. Such patients are at risk for development of Alzheimer's disease.

Mild Cognitive Impairment can be diagnosed and evaluated using any of the many objective tests or criteria well-known and accepted in the fields of psychology or psychiatry.

"Frontotemporal dementia" is a neurodegenerative disease characterized by progressive neuronal loss predominantly involving the frontal and/or temporal lobes. It is distinguished from Alzheimer's disease and Lewy body dementia based on the fact that it does not manifest with amyloid plaques, neurofibrillary tangles, or Lewy bodies. The term "frontotemporal lobar degeneration" or "FTLD" is used to describe the specific pathological diseases that result in frontotemporal dementia syndromes. These are united by their impact on frontal and temporal brain structures. Subtyping is based on the specific proteins found within neuronal inclusions. Most degeneration subtypes are either FTLD-tau, which includes Pick's disease, CBD and PSP, all of which show tau-containing inclusions or FTLD-TDP, which includes several subtypes in which TDP-43 containing inclusions are seen.

Additional Therapeutic Uses

In some embodiments, a peptide of the invention may be used to deliver a therapeutic agent. Thus, for example, in some embodiments, a peptide may be linked to an agent such as a toxin or radiolabel to treat cancer. Any type of cancer can be treated.

In other embodiments, the polypeptides of the present invention are used to reduce or prevent the formation of oxidized phospholipids. In such methods, the polypeptides of the present invention can be administered to a human or non-human animal to reduce or prevent the formation of oxidized phospholipids, thereby inhibiting or preventing a symptom of a disease such as polymyalgia rheumatica, polyarteritis nodosa, scleroderma, idiopathic pulmonary fibrosis, chronic obstructive pulmonary disease, AIDS, coronary calcification, calcific aortic stenosis, osteoporosis and the like.

Typically, all of the above methods involve the administration of a single polypeptide of this invention or, alternatively, the administration of two or more different polypeptides of this invention. Such polypeptides can be administered alone or in combination with other therapeutic agents, such as those disclosed herein. The polypeptides can be provided as monomers or in dimeric, oligomeric or polymeric forms. In certain embodiments, the multimeric forms may comprise associated monomers (e.g., ionically or hydrophobically linked); whereas, in other embodiments, other multimeric forms comprise covalently linked monomers (directly linked or through a linker).

In addition, although all of the foregoing methods are described herein with respect to humans, it will be readily apparent to those of skill that such methods are also useful for other animals, i.e., for veterinary use. Thus, preferred organisms include, but are not limited to, humans, non-human primates, canines, equines, felines, porcines, ungulates, largomorphs, and the like.

Stabilization of Vulnerable Plaques

In some embodiments, polypeptides of the present invention can stabilize vulnerable plaques prone to rupture potentially causing thrombotic arterial occlusion, e.g., by reducing plaque lipid content through reverse cholesterol transport. Thus, in another embodiment, the present invention provides methods for stabilizing a vulnerable plaque in a blood vessel of a mammal by administering to the mammal (and, more preferably, a human), one or more of the polypeptides of this invention (or peptidomimetics of such polypeptides). A "vulnerable" plaque is generally defined as a lipid-rich plaque with a thinned fibrous cap lacking proper collagen and smooth muscle cell support. A mammal, preferably a human, can be diagnosed as having one or more vulnerable plaques using known methods, including temperature detection strategies, labeling strategies, imaging strategies (e.g., devices utilizing magnetic resonance, ultrasound, infra-red, fluorescence, visible light, radio waves, x-ray, etc.), general strategies for discriminating the vulnerable plaque from surround healthy vascular tissue and the like (see, e.g., U.S. Pat. Nos. 6,245,026, 6,475,159, 6,475,210 and 7,118,567). In another embodiment, the mammal, preferably a human, is at risk of having one or more vulnerable plaques. In this embodiment, a clinical symptom has developed and/or a clinical event has occurred that leads one of skill in the art to believe that the mammal is at risk of having one or more vulnerable plaques.

Combination Therapy

In some embodiments, the polypeptides or peptidomimetics of the present invention are administered in combination with one or more additional therapeutic agents for treating or preventing diseases and disorders associated with dyslipidemia, hypercholesterolemia and inflammation, such as cardiovascular disease, including atherosclerosis. For instance, in one embodiment, a polypeptide of the present invention is administered in conjunction with any of the standard treatments for atherosclerosis including, for example, statins (e.g., atorvastatin, lovastatin, pravastatin, simvastatin, fluvastatin, or rosuvastatin); a Nieman-Pick C1-Like 1 sterol transporter channel inhibitor (e.g., Ezetimibe); bile acid binders (e.g., cholestyramine or colestipol); platelet clumping inhibitors (e.g., aspirin, ticlopidine, or clopidogrel); niacin/nicotinamide; PPAR activators; Vitamin E; surgical intervention (e.g., angioplasty, stents, stents, or endarterectomy); and lifestyle changes (e.g., low-fat diets, weight loss, and exercise).

More particularly, the polypeptides or peptidomimetics of the present invention can be used in combination, either as separate units or fixed combinations, with one or more of the following: an antibody which binds to an unwanted inflammatory molecule or cytokine such as interleukin-6, interleukin-8, granulocyte macrophage colony stimulating factor, and tumor necrosis factor-α; an enzyme inhibitor such as a protease inhibitor aprotinin or a cyclooxygenase inhibitor; an antibiotic such as amoxicillin, rifampicin, erythromycin; an antiviral agent such as acyclovir; a steroidal anti-inflammatory such as a glucocorticoid; a non-steroidal anti-inflammatory such as aspirin, ibuprofen or acetaminophen; or a non-inflammatory cytokine such as interleukin-4 or interleukin-10. Other cytokines and growth factors such as interferon-β, tumor necrosis factors, antiangiogenic factors, erythropoietins, thrombopoietins, interleukins, maturation factors, chemotactic protein, and their variants and derivatives that retain similar physiological activities may also be used as an additional therapeutic agents.

The polypeptides or peptidomimetics of the present invention can be used in combination with drugs commonly used to treat lipid disorders in, for example, diabetic patients. Such drugs include, but are not limited to, HMG-CoA reductase inhibitors, PCSK9 inhibitors, nicotinic acid, ezetimide, bile acid sequestrants, fibric acid derivatives, MTP inhibitor, ACAT inhibitor and CETP inhibitors. Examples of HMG-CoA reductase inhibitors include lovastatin, pravastatin, simvastatin, rosuvastatin, fluvastatin and atorvastatin. Examples of bile acid sequestrants include cholestyramine, colestipol and colesevelam. Examples of fibric acid derivatives include gemfibrozil and fenofibrate, The polypeptides or peptidomimetics of the invention can also be used in combination with anti-hypertensive drugs, such as, for example, diuretics, β-blockers, cathepsin S inhibitors, methyldopa, α2-adrenergic agonists, guanadrel, reserpine, β-adrenergic receptor antagonists, α1-adrenergic receptor antagonists, hydralazine, minoxidil, calcium channel antagonists, ACE inhibitors and angiotensin II-receptor antagonists. Examples of β-blockers include acebutolol, bisoprolol, esmolol, propanolol, atenolol, labetalol, carvedilol and metoprolol. Examples of ACE inhibitors include captopril, enalapril, lisinopril, benazepril, fosinopril, ramipril, quinapril, perindopril, trandolapril and moexipril.

The polypeptides or peptidomimetics of the invention can also be used in combination with cardiovascular drugs such as calcium channel antagonists, β-adrenergic receptor antagonists and agonists, aldosterone antagonists, ACE inhibitors, angiotensin II receptor antagonists, nitrovasodilators, and cardiac glycosides. The polypeptides or peptidomimetics of the invention can also be used in combination with anti-inflammatory drugs such as H1-receptor antagonists, H2-receptor mediated agonists and antagonists, COX-2 inhibitors, NSAID, salicylates, acetaminophen, propionic acid derivatives, enolic acids, diaryl substituted fuanones, cyclooxygenase inhibitors, and bradykinin agonists and antagonists.

Other therapeutic agents suitable for use in combination with the polypeptides or peptidomimetics of the present invention are disclosed in U.S. Patent Application Publication No. 2005/0142180, the teachings of which are incorporated herein by reference.

The polypetide (or peptidomimetics thereof) and the additional therapeutic agent can be administered simultaneously or sequentially. For example, the polypeptide may be administered first, followed by the additional therapeutic agent. Alternatively, the additional therapeutic agent may be administered first, followed by the polypeptide of the invention. In some cases, the polypeptide of the invention and the additional therapeutic agent are administered in the same formulation. In other cases, the polypeptide and the additional therapeutic agent are administered in different formulations. When the polypeptide and the additional therapeutic agent are administered in different formulations, their administration may be simultaneous or sequential.

Pharmaceutical Formulations

In order to carry out the methods of the invention, one or more polypeptides of this invention or peptidomimetics thereof are typically administered to an individual diagnosed as having or at risk of having a disease or disorder associated with dyslipidemia or hypercholesterolemia (e.g., to an individual diagnosed as having one or more symptoms of atherosclerosis, or as being at risk for atherosclerosis); or a disease associated with abnormal glucose metabolism; or Alzheimer's Disease. The polypeptides or peptidomimetics thereof can be administered in their "native" form or, if desired, in the form of, for example, salts, esters, amides, prodrugs, derivatives, and the like, provided that the salt, ester, amide, prodrug or derivative is suitable pharmacologically, i.e., effective in the methods of the present invention.

In one embodiment of the methods described herein, the route of administration can be oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or otic delivery, or any other methods known in the art as one skilled in the art may easily perceive. Other embodiments of the compositions of the invention incorporate particulate forms protective coatings, protease inhibitors or permeation enhancers for various routes of administration, including parenteral, pulmonary, nasal and oral. The pharmaceutical compositions can be administered in a variety of unit dosage forms depending upon the method/mode of administration. Suitable unit dosage forms include, but are not limited to, powders, tablets, pills, capsules, lozenges, suppositories, patches, nasal sprays, injectibles, implantable sustained-release formulations, etc.

As such, in another aspect, the present invention provides pharmaceutical compositions comprising a pharmaceutically effective amount of a polypeptide or peptidomimetic of the present invention and an acceptable carrier and/or excipients. A pharmaceutically acceptable carrier includes any solvents, dispersion media, or coatings that are physiologically compatible and that preferably does not interfere with or otherwise inhibit the activity of the polypeptide or peptidomimetic. Preferably, the carrier is suitable for intravenous, intramuscular, oral, intraperitoneal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers.

Other physiologically acceptable compounds include, but are not limited to, wetting agents, emulsifying agents, dispersing agents or preservatives which are particularly useful for preventing the growth or action of microorganisms. Various preservatives are well known and include, for example, phenol and ascorbic acid. One skilled in the art will appreciate that the choice of pharmaceutically acceptable carrier(s), including a physiologically acceptable compound depends, for example, on the route of administration of the polypeptide(s) or peptidomimetic(s) and on the particular physio-chemical characteristics of the polypeptide(s) or peptidomimetic(s).

In a preferred embodiment, the pharmaceutically acceptable carrier is physiological saline. Other pharmaceutically acceptable carriers and their formulations are well-known and generally described in, for example, Remington's Pharmaceutical Science (22nd Ed., Allen, Loyd V., editor-in-chief, 2012). Various pharmaceutically acceptable excipients are well-known in the art and can be found in, for example, Handbook of Pharmaceutical Excipients (seventh edition, 2012.). Again, the pharmaceutical composition can be formulated as a solution, microemulsion, liposome, capsule, tablet, or other suitable form. The active component may be coated in a material to protect it from inactivation by the environment prior to reaching the target site of action.

In certain embodiments, the polypeptides or peptidomimetics of this invention can be administered orally (e.g., via a tablet) or as an injectable in accordance with standard methods well known to those of skill in the art. In other preferred embodiments, the polypeptides or peptidomimetics can also be delivered through the skin using conventional transdermal drug delivery systems. Other formulations for topical drug delivery include, but are not limited to, ointments and creams.

In some embodiments, implanted devices (e.g., arterial and intravenous stents, including eluting stents, and catheters) are used to deliver the formulations comprising the polypeptides and peptidomimetics of the invention. For example, aqueous solutions comprising the polypeptides and peptidomimetics of the invention are administered directly through the stents and catheters. In some embodiments, the stents and catheters may be coated with formulations comprising the polypeptides and peptidomimetics described herein. In some embodiments, the polypeptides and peptidomimetics will be in time-release formulations an eluted from the stents. Suitable stents are described in, e.g., U.S. Pat. Nos. 6,827,735; 6,827,735; 6,827,732; 6,824,561; 6,821,549; 6,821,296; 6,821,291; 6,818,247; 6,818,016; 6,818,014; 6,818,013; 6,814,749; 6,811,566; 6,805,709; 6,805,707; 6,805,705; 6,805,704; 6,802,859; 6,802,857; 6,802,856; and 49 6,802,849. Suitable catheters are described in, e.g., U.S. Pat. Nos. 6,829,497; 6,827,798; 6,827,730; 6,827,703; 6,824,554; 6,824,553; 6,824,551; 6,824,532; and 6,819,951.

Polypeptides of this comprising L-form or D-form amino acids can be administered without protection against proteolysis by stomach acid, etc. Nevertheless, in certain embodiments, polypeptide delivery can be enhanced by the use of protective excipients, as known in the art (see, e.g., U.S. Pat. No. 5,391,377).

In certain embodiments of the present invention, the pharmaceutical compositions are sustained release formulations. Polypeptides or peptidomimetics of the present invention may be admixed with biologically compatible polymers or matrices that control the release rate of the copolymers into the immediate environment. Controlled or sustained release compositions include formulation in lipophilic depots (e.g., fatty acids, waxes, oils). Also contemplated by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral. Acceptable carriers include carboxymethyl cellulose (CMC) and modified CMC. In one embodiment, elevated serum half-life is maintained using a biodegradable microsphere delivery system for proteins and polypeptides is used (Tracy, *Biotechnol. Prog.*, 14:108 (1998); Johnson et al., *Nature Med.*, 2:795 (1996); Herbert et al., *Pharmaceut. Res.*, 15:357 (1998)), which involves the use of a dry powder composed of biodegradable polymeric microspheres containing the polypeptide in a polymer matrix that can be compounded as a dry formulation with or without other agents.

In another embodiment, one or more components of the solution can be provided as a concentrate, e.g., in a storage container ready for dilution, or in a soluble capsule ready for addition to a volume of water.

A pharmaceutical composition of the present invention is preferably sterile and non-pyrogenic at the time of delivery, and is preferably stable under the conditions of manufacture and storage. These pharmaceutical compositions can be sterilized by conventional, well known sterilization techniques.

In therapeutic applications, the compositions of this invention are administered to an individual diagnosed as having or at risk of having a disease or disorder associated with dyslipidemia, hypercholesterolemia and inflammation (and, in preferred embodiments, to an individual diagnosed as having one or more symptoms of atherosclerosis or as being at risk for atherosclerosis) or a disease associated with abnormal glucose metabolism, or Alzheimer's Disease, in an amount sufficient to cure or at least partially prevent or arrest the disease, condition and/or its complications. An amount adequate to accomplish this is defined as a "therapeutically effective dose." Amounts effective for this use will depend upon the severity of the disease and the general state of the patient's health. Single or multiple administrations of the compositions can be administered depending on the dosage and frequency as required and tolerated by the patient. In any event, the composition should provide a sufficient quantity of the active agents, i.e., polypeptides or peptidomimetics, of the formulations of this invention to effectively treat (ameliorate one or more symptoms) the individual or patient.

The concentration of polypeptide or peptidomimetic can vary widely, and will be selected primarily based on fluid volumes, viscosities, body weight, circulating plasma levels of the polypeptide, polypeptide toxicities, progression of the disease (e.g., atherosclerosis), the production of antibodies that specifically bind to the polypeptide, and the like in accordance with the particular mode of administration selected and the patient's needs. Typically, the dose equivalent of a polypeptide or peptidomimetic is from about 0.1 to about 50 mg per kg, preferably from about 1 to about 25 or 30 mg per kg, or from about 1 to about 20 mg per kg body weight. It will be appreciated that such dosages may be varied to optimize a therapeutic regimen in a particular subject or group of subjects.

For administration, polypeptides of the present invention can be administered at a rate determined by the LD50 of the polypeptide, and the side-effects of the polypeptide at various concentrations, as applied to the mass and overall health of the patient. Administration can be accomplished via single or divided doses, e.g., doses administered on a regular basis (e.g., daily) for a period of time (e.g., 2, 3, 4, 5, 6, days or 1-3 weeks or more).

As explained herein, the polypeptides or peptidomimetics of the present invention can be modified in a number of different ways. For instance, the polypeptides can be modified so that the R-groups on the constituent amino acids and/or the terminal amino acids are blocked, i.e., protected, by a protecting group. It has been found that blockage, particularly of the amino and/or carboxy termini, can greatly improve oral delivery and significantly increases serum half-life. In addition, to enhance delivery and/or biological activites in vivo, salts, esters, amides, prodrugs and other derivatives of the polypeptides or peptidomimetics of the present invention can be prepared using standard procedures known to those skilled in the art of synthetic organic chemistry and described, for example, by March (1992) Advanced Organic Chemistry; Reactions, Mechanisms and Structure, 4th Ed. N.Y. Wiley-Interscience.

The foregoing formulations and administration methods are clearly intended to be illustrative and not limiting in any way. It will be appreciated that, using the teaching provided herein, other suitable formulations and modes of administration can be readily devised.

Lipid-Based Formulations

In another aspect, the polypeptides and peptidomimetics of the present invention are preferably administered in conjunction with one or more lipids. The lipids can be formulated as an excipient to protect and/or enhance transport/uptake of the polypeptides or peptidomimetics or they can be administered separately.

The lipids can be formulated into liposomes, nanocapsules, microparticles, microspheres, lipids particles, lipid vesicles and the like. Such lipid formulations can be used to encapsulated the polypeptides and peptidomimetics of the present invention and/or they can be simply complexed/ admixed with such polypeptides and peptidomimetics. Those of skill in the art will know how to use such lipid formulations to either encapsulate or complex the polypeptides or peptidomimetics of the present invention. For instance, the formation and use of liposomes is generally known to those of skill in the art. For example, liposomes with improved serum stability and circulation half-times (see, U.S. Pat. No. 5,741,516) may be used. Further, various methods of liposome and liposome-like preparations as potential drug carriers have been reviewed (see, U.S. Pat. Nos. 5,567,434; 5,552,157; 5,565,213; 5,738,868 and 5,795, 587).

In one embodiment, the polypeptides or peptidomimetics of the present invention are complexed with a lipid, such as a phospholipid (e.g., 1-palmitoyl-2-oleoyl-sn-glycerol-phosphatidylcholine ("POPC") in a manner similar to that disclosed in U.S. Patent Application Publication No. 2005/ 0142180, which was published Jun. 30, 2005, the teachings of which are incorporated herein by reference. As such, the present invention provides polypeptide-lipid complexes (or, alternatively, peptidomimetic-lipid complexes) having an increased ability to efflux cholesterol from cells. Typically, the lipid is mixed with the polypeptide prior to administration. The polypeptides of the present invention and lipids can be mixed in an aqueous solution in appropriate ratios and can be complexed by methods known in the art, including, but not limited to, freeze-drying, detergent solubilization followed by dialysis, microfluidization, sonication, and homogenization. Complex efficiency can be optimized, for example, by varying pressure, ultrasonic frequency or detergent concentration. An example of a detergent commonly used to prepare polypeptide-lipid complexes is sodium cholate.

In certain embodiments, the polypeptide-lipid (e.g., phospholipids) complex can be in solution with an appropriate pharmaceutical diluent or carrier. In other embodiments, freeze-dried or lyophilized preparations of the polypeptide-lipid complexes can be hydrated or reconstituted with an appropriate pharmaceutical diluent prior to administration. In another embodiment, the polypeptide-lipid complexes can be frozen preparations that are thawed until a homogenous solution is achieved prior to administration to a subject in need thereof.

The lipid can be any suitable lipid known to those of skill in the art. In one embodiment, non-phosphorus containing lipids can be used, including stearylamine, dodecylamine, acetyl palmitate, (1,3)-D-mannosyl-(1,3)digly-ceride, aminophenylglycoside, 3-cholesteryl-6'-(glycosylthio)hexyl ether glycolipids, N-(2,3-di(9-(Z)-octadecenyloxy))-prop-1-yl-N,N,N-trimethylammonium chloride and fatty acid amides.

In another embodiment, a phospholipids or a mixture of phospholipids is used.

Suitable phospholipids include, but are not limited to, can be a small alkyl chain phospholipid, phosphatidylcholine, egg phosphatidylcholine, soybean phosphatidylcholine, dipalmitoylphosphatidylcholine, soy phosphatidylglycerol, egg phosphatidylglycerol, distearoylphosphatidylgly-cerol, dimyristoylphosphatidylcholine, distearoylphosphatidyl-choline, dilaurylphosphatidylcholine, 1-myristoyl-2-palmi-toylphosphatidylcholine, 1-palmitoyl-2-myristoylphosphati-dylcholine, 1-palmitoyl-2-stearoylphospha-tidylcholine, 1-stearoyl-2-palmitoylphosphatidylcholine, dioleoylphosphatidylcholine, 1-palmitoyl-2-oleoylphosphatidylcholine, 1-oleoyl-2-palmitylphosphatidylcholine, dioleoylphosphatidylethanolamine, dilauroylphosphatidylglycerol, phosphatidylserine, phosphatidylethanolamine, phosphatidylinositol, phosphatidylglycerol, diphosphatidylglycerol, dimyristoylphosphatidylglycerol, dipalmitoylphosphatidylglycerol, distearoylphosphatidylglycerol, dioleoylphosphatidylglycerol, phosphatidic acid, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, sphingomyelin, sphingolipids, brain sphingomyelin, dipalmitoylsphingomyelin, distearoylsphingomyelin, galactocerebroside, gangliosides, cerebrosides, phosphatidylglycerol, phosphatidic acid, lysolecithin, lysophosphatidylethanolamine, cephalin, cardiolipin, dicetylphosphate, distearoyl-phosphatidylethanolamine and cholesterol and its derivatives. Similarly, the phospholipid can be a derivative or analogue of any of the foregoing phospholipids or, again, a mixture of two or more of any of the foregoing phospholipids. Such phospholipids can be obtained from commercial sources, natural sources or by synthetic or semi-synthetic means known to those of skill in the art.

In some embodiments, the polypeptide-lipid complex is a polypeptide-phospholipid-complex. For example, in one embodiment, the lipid is 1-POPC or ("1-palmitoyl-2-oleoyl-sn-glycero-3-phosphocholine").

It will be readily apparent to those of skill in the art that the complex comprising a polypeptide of the present invention and a lipid, preferably a phospholipids, can comprise any amount of lipid and any amount of the polypeptide, provided the complex is effective to mediate cholesterol efflux and, in turn, to treat diseases or symptoms associate therewith. As previously mentioned, it has surprisingly been found that when the polypeptides of the present invention are complexed with, for example, POPC at ratios ranging from about 1:0.5 to about 1:5 (polypeptide:POPC), distinct lipid-polypeptide particles are formed having sizes of between about 5 and about 20 nm, which result in a significantly enhanced capacity, i.e., ability, to efflux cholesterol from cells. However, the polypeptide-lipid complexes of the present invention can comprise complexes with other ratios of phospholipid to polypeptide, such as about 100:1, about 10:1, about 5:1, about 3:1, about 2:1, about 1:1, about 1:2, about 1:3, about 1:5, about 1:10 and about 1:100 (wt of polypeptide/wt of lipid).

The polypeptide-lipid complexes of the present invention can be made by any method known to one of skill in the art. In some cases, it is desirable to mix the lipid and the polypeptide prior to administration. Lipids can be in solution or in the form of liposomes or emulsions formed using standard techniques, such as homogenization, sonication or extrusion. For example, a polypeptide of the present invention (e.g., a polypeptide of SEQ ID NO:1 or SEQ ID NO:2, or a variant thereof) can be co-sonicated (using a bath or probe sonicator) with the appropriate lipid to form the polypeptide-lipid complexes. In certain embodiments, the polypeptide can be combined with preformed lipid vesicles resulting in the spontaneous formation of a polypeptide-lipid complex. In another embodiment, the polypeptide-lipid complex can also be made by a detergent dialysis method. In this method, a mixture of the polypeptide, lipid and a detergent, such as sodium cholate, can be dialyzed to remove the detergent and reconstituted to make the polypeptide-lipid complexes (see, e.g., Jonas et al., *Methods Enzymol.*, 128: 553-82 (1986)).

In other embodiments, the polypeptide-lipid complexes can be made by co-lyophilization as described in U.S. Pat. Nos. 6,287,590 and 6,455,088, the teachings of both of which are hereby incorporated by reference in their entirety. Other methods are disclosed in, for example, U.S. Pat. Nos. 6,004,925, 6,037,323 and 6,046,166, the teachings of all of which are incorporated herein by reference in their entireties. Other methods of preparing polypeptide-lipid complexes will be apparent to those of skill in the art.

In one preferred embodiment, the polypeptide-lipid complexes can be made by homogenization.

Nucleic Acids

In another embodiment, the present invention provides isolated nucleic acids encoding the polypeptides disclosed herein, expression vectors comprising the nucleic acids, and host cells comprising the expression vectors. More particularly, the present invention provides isolated nucleic acids encoding the polypeptides of the present invention having cholesterol efflux activities similar to full-length apolipoproteins, on a per molecule basis, and having high selectivity for ABACI in a manner similar to full-length apolipoproteins, the polypeptides including, but not limited to, polypeptides having an amino acid sequence of SEQ ID NO:1 or SEQ ID NO:2, or a variant as described herein.

In certain embodiments, nucleic acids encoding the polypeptides of the invention are used for transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acids, under the control of a promoter, then express a polypeptide of the present invention, thereby mitigating the effects of a disease associated with dyslipidemia, hypercholesterolemia, inflammation, abnormal glucose metabolism, or Alzheimer's Disease.

Use as Research Tools and in Methods of Diagnosis

The polypeptides and peptidomimetics of the invention are also useful as research tools.

In some cases, the polypeptides or peptidomimetics of the invention are used to target therapeutic agents to cells and tissues expressing ABCA.

In other embodiments, the polypeptides or peptidomimetics of the invention can be used in methods of diagnosing diseases and disorders associated with aberrant cholesterol efflux or with ABCA. For example, the peptides can be used in assays to diagnose reverse cholesterol transport deficiency and to identify individuals predicted to be responders to peptide treatment. Such diagnostic assays include in vitro assays. For example, cholesterol efflux can be evaluated in an assay in which a polypeptide of the invention is mixed with plasma from a subject and exposed to cells to indicate whether a subject would respond to treatment (e.g., a large increase in efflux in the presence of the peptide compared with plasma-mediated efflux in the absence of the peptide suggests that the subject would be responsive). Similarly, a polypeptide of the invention can be mixed with plasma from a subject to detect changes in HDL subclass distribution and/or to detect changes in anti-oxidative properties of the plasma in the presence of the peptide.

In some embodiments, the polypeptides or peptidomimetics are used for in vivo imaging methods. The polypeptides or peptidomimetics are conjugated to a detectable moiety and administered to a subject (e.g., a mammal such as a human). Detection of the detectable moiety allows imaging of a cell, tissue, or organ of interest, including, e.g., an atherosclerotic lesion or an amyloid plaque.)

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results.

EXAMPLES

This example shows reduction in toxicity of a peptide (ATI-5261) by inversion of salt bridges within the peptide.

FIG. 1—Evidence that positively charged amino acids associated with Class A α-helix structure contribute to the toxic effects of ATI-5261. Aromatic F residues in ATI-5261 promote toxicity, which suggests that interactions of ATI-5261 with cellular membranes may be involved. Since the position of positively charged amino acids near the lipid-water interface of class A α-helices is thought to mediate membrane interactions, we tested whether inverting the positions of positive and negative residues within ATI-5261 lessened the toxic response of the peptide at high doses. Panel A—Helical-wheel and -net diagrams of ATI-5261 showing the positions of positively charged lysine (K) and arginine (R) at the lipid interface of the amphipathic α-helix (i.e. helical wheel diagrams on left). Panel B—Peptide analogs of ATI-5261 with charge-inversions created by switching the positions of positive and negative amino acids within each of the peptides putative salt-bridges (shaded circles in helical-net diagram, i.e. positions i and i+4). Panel C—Figure showing that charge-inversion eliminates the cytotoxicity and TG elevating activity of ATI-5261. Male Chow-fed C57Bl/6 mice were injected IP with 300 mg/kg ATI-5261 and its charge inversion analog (T5657-10). Plasma CPK, ALT, AST and TG (table) were assessed after 4 h as described in FIGS. 4-6. Values and means±SD, n=4. Moving the positively charged residues away from the lipid surface eliminated nearly all the cytotoxic and TG elevating activity of the ATI-5261, i.e. even in the presence of aromatic F residues. Thus the position of positively charged residues together with the presence of aromatic phenylalanine appears necessary to induce cytotoxicity, but each is not sufficient to induce such a response.

Figure 2:
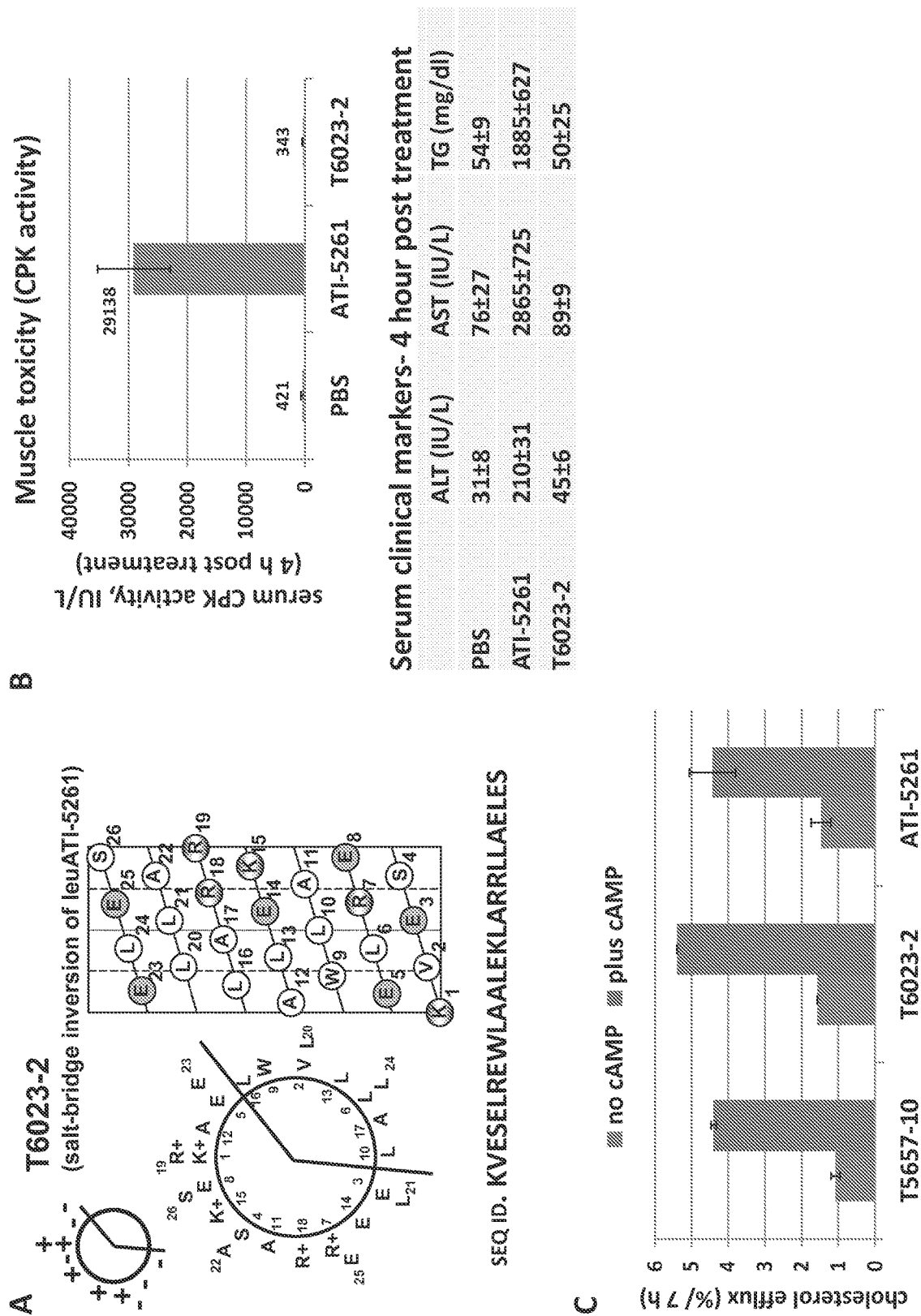
FIG. 2—Charge-inversion eliminates the residual toxicity associated with the aliphatic analog LeuATI-5261. Panel A—The positions of charged amino acids within the LeuATI-5261 peptide were switched to move the positive lysine and arginine residues away from the lipid-water interface of the amphipathic α-helix. Panel B— Safety and TG elevating effects were evaluated by injecting (IP) peptides (300 mg/kg) into male, chow-fed C57Bl/6 mice. Values are means SD, n=4. The parent ATI-5261 peptide with class A structure induced high-levels of plasma CPK, AST, and TG by 4 h. In contrast, the leucine peptide analog with positive charge-inversion (T6023-2, SEQ ID NO:35) displayed no increase in muscle toxicity or elevated plasma enzymes compared to vehicle alone. Panel C— Analogs of ATI-5261 and the LeuATI-5261 peptide retained ability to stimulate ABCA1 dependent cholesterol efflux with high efficiency. J774 macrophages were labeled with [3H]cholesterol and treated with (red, right side bars) and without (blue, left side bars) cAMP to modulate ABCA1 expression. Peptides of either ATI-5261 or the Leu.ATI-5261 analog with charged inversions stimulated high-levels of cholesterol efflux at a saturating concentration of 3 µg/ml, similar to that seen using the parent ATI-5261 peptide.

FIG. 2—Charge-inversion eliminates the residual toxicity associated with the aliphatic analog LeuATI-5261. Panel A—The positions of charged amino acids within the LeuATI-5261 peptide were switched to move the positive lysine and arginine residues away from the lipid-water interface of the amphipathic α-helix. Panel B—Safety and TG elevating effects were evaluated by injecting (IP) peptides (300 mg/kg) into male, chow-fed C57Bl/6 mice. Values are means SD, n=4. The parent ATI-5261 peptide with class A structure induced high-levels of plasma CPK, AST, and TG by 4 h. In contrast, the leucine peptide analog with positive charge-inversion (T6023-2) displayed no increase in muscle toxicity or elevated plasma enzymes compared to vehicle alone. Panel C—Analogs of ATI-5261 and the LeuATI-5261 peptide retained ability to stimulate ABCA1 dependent cholesterol efflux with high efficiency. J774 macrophages were labeled with [3H]cholesterol and treated with (red, right side bars) and without (blue, left side bars) cAMP to modulate ABCA1 expression. Peptides of either ATI-5261 or the Leu.ATI-5261 analog with charged inversions stimulated high-levels of cholesterol efflux at a saturating concentration of 3 μg/ml, similar to that seen using the parent ATI-5261 peptide.

FIG. 3—Toxic properties of lysine residues in ATI-5261—To test whether the cytotoxic response of ATI-5261 was preferentially linked to arginine or lysine residues, peptide analogs of ATI-5261 with lysine eliminations, R→K substitutions, or partial charge inversion were created. Panel A—Safety and TG elevating effects were evaluated by injecting (IP) peptides (300 mg/kg) into male, chow-fed C57Bl/6 mice. Values are means SD, n=4. Removal of lysine25 from C-terminal end of ATI-5261, by either ablation (T5766-5) or amino acid substitution (K25→N, T5594-4) greatly reduced muscle toxicity as judged by decreased CPK activity in plasma (left panel), suggesting lysine residues promote toxicity. Peptides with either all lysine residues (i.e. R→K substitutions, T5594-5) or partial charged inversion also displayed cytotoxic and TG elevating activity, consistent with role of either lysine or arginine in mediating negative effects of the peptides. Panel B-ABCA1-dependent cholesterol efflux activity of peptides determined using J774 macrophages labeled with [3H]cholesterol. Results are expressed as the ABCA1 component of efflux. All peptides were functional and stimulated high-levels of cholesterol efflux at a saturating concentration of 3 μg/ml, similar to that seen using the parent ATI-5261 peptide.

Inverting the salt bridges can also be used to reduce toxicity of a peptide having the sequence of ATI-5261 in reverse, as salt bridge inversion also moves the positively charged residues away from the lipid surface in the reversed peptide.

As noted above, the entirety of PCT application number PCT/US2014/029232, including the examples section, is incorporated by reference herein.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, publications, and accession numbers are incorporated herein by reference for all purposes.

What is claimed is:

1. An isolated peptide of 100 amino acids or less in length having cholesterol efflux activity, the peptide comprising an amino acid sequence that is an amphipathic α-helix that has a non-polar surface and a polar surface, wherein the polar surface comprises charged and uncharged amino acid residues at the lipid-water interface, wherein the amino acid sequence comprises a 24-amino acid sequence $X_1X_2X_3X_4X_5X_6X_7X_8X_9X_{10}X_{11}X_{12}X_{13}X_{14}X_{15}X_{16}X_{17}X_{18}X_{19}X_{20}X_{21}X_{22}X_{23}X_{24}$, comprising amino acid residues as follows, each position designated by position in the 24-amino acid sequence:

(a) (i) a set of four pairs of salt bridge-forming amino acids: a pair at positions $X_1$ and $X_5$, a pair at positions $X_3$ and $X_7$, a pair at positions $X_{14}$ and $X_{18}$, and a pair at positions $X_{19}$ and $X_{23}$, wherein each pair has a positively charged residue at one position and an acidic residue at the other position to form a salt bridge; and wherein the set of four pairs of amino acids comprise at least one of the following pairs: $X_1$ is a positively charged residue and $X_5$ is an acidic residue, $X_3$ is an acidic residue and $X_7$ is a positively charged residue, $X_{14}$ is an acidic residue and $X_{18}$ is a positively charged residue, or $X_{19}$ is a positively charged residue and $X_{23}$ is an acidic residue;

(ii) one pair of salt bridge-forming amino acids at positions $X_1$ and $X_5$, wherein $X_1$ is a positively charged residue and $X_5$ is an acidic residue, each of positions $X_{17}$, $X_{18}$, and $X_{19}$ are acidic residues, and:
  (1) each of positions $X_3$, $X_{14}$, and $X_{23}$ is independently selected from citrulline, Q, N, Y, W, A, I, L, and V;
  (2) two of three positions $X_3$, $X_{14}$, and $X_{23}$ are independently selected from citrulline, Q, N, Y, W, A, I, L, and V; and the third of the three positions is a positively charged residue; or
  (3) one of three positions $X_3$, $X_{14}$, and $X_{23}$ is independently selected from citrulline, Q, N, Y, W, A, I, L, and V; and the second and third of the three positions are positively charged residues;

(iii) an acidic residue at one of positions $X_1$ and $X_5$ forms a salt bridge with a positively charged residue at the other position of $X_1$ and $X_5$; $X_3$ is an acidic residue and $X_7$ is a positively charged residue and:
  (1) each of two positions $X_{14}$ and $X_{23}$ are independently selected from citrulline, Q, N, Y, W, A, I, L, and V; and position $X_{18}$ and $X_{19}$ are acidic residues;
  (2) position $X_{14}$ is selected from citrulline, Q, N, Y, W, A, I, L, and V; position $X_{18}$ is an acidic residue; and the residues at positions $X_{19}$ and $X_{23}$ form a salt bridge between an acidic residue at one position and a positively charged residue at the other; or
  (3) position $X_{23}$ is selected from citrulline, Q, N, Y, W, A, I, L, and V; position $X_{19}$ is an acidic residue; and the residues at positions $X_{14}$ and $X_{18}$ form a salt bridge between an acidic residue at one position and a positively charged residue at the other;

(iv) an acidic residue at one of positions $X_1$ and $X_5$ forms a salt bridge with a positively charged residue at the other position of $X_1$ and $X_5$; $X_{14}$ is an acidic residue and $X_{18}$ is a positively charged residue, and:
  (1) each of two positions $X_3$ and $X_{23}$ are independently selected from citrulline, Q, N, Y, W, A, I, L, and V; and positions $X_7$ and $X_{19}$ are acidic residues;
  (2) position $X_3$ is selected from citrulline, Q, N, Y, W, A, I, L, and V; position $X_7$ is an acidic residue; and the residues at positions $X_{19}$ and $X_{23}$ form a salt bridge between an acidic residue at one position and a positively charged residue at the other position; or
  (3) position $X_{23}$ is selected from citrulline, Q, N, Y, W, A, I, L, and V; position $X_{19}$ is an acidic residue, and the residues at positions $X_3$ and $X_7$ form a salt bridge between an acidic residue at one position and a positively charged residue at the other position;

(v) an acidic residue at one of positions $X_1$ and $X_5$ forms a salt bridge with a positively charged residue at the other position of $X_1$ and $X_5$; $X_{19}$ is a positively charged residue and $X_{23}$ is an acidic residue, and:
  (1) each of two positions $X_3$ and $X_{14}$ are independently selected from citrulline, Q, N, Y, W, A, I, L, and V; and positions $X_7$ and $X_{18}$ are acidic residues;
  (2) position $X_3$ is selected from citrulline, Q, N, Y, W, A, I, L, and V; and position $X_7$ is an acidic residue; and the residues at positions $X_{14}$ and $X_{18}$ form a salt bridge between an acidic residue at one position and a positively charged residue at the other position; or
  (3) position $X_{14}$ is selected from citrulline, Q, N, Y, W, A, I, L, and V; and position $X_{18}$ is an acidic residue; and the residues at positions $X_3$ and $X_7$ form a salt bridge between an acidic residue at one position and a positively charged residue at the other position;

(b) $X_2$, $X_6$, $X_{10}$, $X_{13}$, $X_{16}$, $X_{17}$, $X_{20}$, $X_{21}$, and $X_{24}$ are each aliphatic residues independently selected from the group consisting of L, V, A, and I;

(C) $X_9$ is W, L, or F;

(d) $X_4$, $X_{11}$, and $X_{22}$ are independently selected from S, T, G, A, and Y;

(e) $X_8$ and $X_{15}$ is E, D, K, or R; and (f) $X_{12}$ is A, V, L, I, or F.

2. The isolated peptide of claim 1, wherein $X_9$ is W.

3. The isolated peptide of claim 1, wherein $X_{10}$, $X_{13}$, $X_{16}$, and $X_{20}$ are independently selected from the group consisting of L, V, and I.

4. The isolated peptide of claim 1, wherein the 24-amino acid sequence comprises:

(a) a positively charged residue at position $X_1$, an acidic residue at position $X_5$, and positions $X_3$, $X_{14}$, and $X_{23}$ are independently selected from citrulline, Q, N, Y, W, A, I, L, and V;

(b) an acidic residue at position $X_3$, a positively charged residue at position $X_7$; and position $X_{14}$ and position $X_{23}$ are independently selected from citrulline, Q, N, Y, W, A, I, L, and V;

(c) an acidic residue at position $X_{14}$, a positively charged residue at position $X_{18}$, and position $X_3$ and position $X_{23}$ are independently selected from citrulline, Q, N, Y, W, A, I, L, and V; or (d) a positively charged residue at position $X_{19}$, an acidic residue at position $X_{23}$, and position $X_3$ and position $X_{14}$ are independently selected from citrulline, Q, N, Y, W, A, I, L, and V.

5. The isolated peptide of claim 1, wherein:

the 24-amino acid sequence has at least 60% identity to any one of the following amino acid sequences:

```
                                           (SEQ ID NO: 1)
KVRSELEEWLAALRELAEELLARL, (SEQ ID NO: 2)
EVESKLREWLAALRELAEELLARL, (SEQ ID NO: 3)
EVRSKLEEWLAALEELARELLARL, (SEQ ID NO: 4)
EVRSKLEEWLAALRELAERLLAEL, (SEQ ID NO: 5)
KVESELREWLAALRELAEELLARL (SEQ ID NO: 6)
KVRSELEEWLAALEELARELLARL (SEQ ID NO: 7)
KVRSELEEWLAALRELAERLLAEL (SEQ ID NO: 8)
EVESKLREWLAALEELARELLARL
```

```
                                           (SEQ ID NO: 9)
EVESKLREWLAALRELAERLLAEL,
or (SEQ ID NO: 10)
EVRSKLEEWLAALEELARRLLAEL.
```

6. The isolated polypeptide of claim 1, wherein the peptide further comprises a protecting group.

7. The isolated peptide in accordance with claim 1, wherein all enantiomeric amino acids are "D" amino acids, or enantiomeric amino acids are a mixture of "L" amino acids and "D" amino acids.

8. The isolated peptide of claim 1, wherein the positively charged amino acid residue of (a) is an R or K and the acidic residue of (a) is a D or E.

9. The isolated peptide of claim 1, wherein $X_9$ is W, $X_4$ is S, $X_{11}$ is A, $X_{22}$ is A, and $X_8$ is E or D.

10. The isolated peptide of claim 1, wherein $X_8$ is E or D and $X_{15}$ is K or R.

11. The isolated peptide of claim 1, comprising the amino acid sequence of any one of SEQ ID NOS:1-10.

12. The isolated peptide of claim 1, comprising the amino acid sequence of SEQ ID NO:35.

13. A composition comprising a peptide of claim 1 and a pharmaceutically acceptable carrier.

14. A composition comprising a peptide of claim 1 complexed with a lipid.

15. A method for mediating cholesterol efflux in a mammal in need thereof, said method comprising administering to said mammal a peptide of claim 1, whereby cholesterol efflux is mediated.

16. The method in accordance with claim 15, wherein said mammal is a human.

* * * * *

SEQUENCE LISTING

```
<160> NUMBER OF SEQ ID NOS: 40

<210> SEQ ID NO 1
<211> LENGTH: 24
<212> TYPE: PRT
<213> ORGANISM: Artificial Sequence
<220> FEATURE:
<223> OTHER INFORMATION: synthetic peptide construct
```

```
<400> SEQUENCE: 1

Lys Val Arg Ser Glu Leu Glu Glu Trp Leu Ala Ala Leu Arg Glu Leu
1               5                   10                  15

Ala Glu Glu Leu Leu Ala Arg Leu
            20

<210> SEQ ID NO 2
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 2

Glu Val Glu Ser Lys Leu Arg Glu Trp Leu Ala Ala Leu Arg Glu Leu
1               5                   10                  15

Ala Glu Glu Leu Leu Ala Arg Leu
            20

<210> SEQ ID NO 3
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 3

Glu Val Arg Ser Lys Leu Glu Glu Trp Leu Ala Ala Leu Glu Glu Leu
1               5                   10                  15

Ala Arg Glu Leu Leu Ala Arg Leu
            20

<210> SEQ ID NO 4
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 4

Glu Val Arg Ser Lys Leu Glu Glu Trp Leu Ala Ala Leu Arg Glu Leu
1               5                   10                  15

Ala Glu Arg Leu Leu Ala Glu Leu
            20

<210> SEQ ID NO 5
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 5

Lys Val Glu Ser Glu Leu Arg Glu Trp Leu Ala Ala Leu Arg Glu Leu
1               5                   10                  15

Ala Glu Glu Leu Leu Ala Arg Leu
            20

<210> SEQ ID NO 6
<211> LENGTH: 24
<212> TYPE: PRT
<213> ORGANISM: Artificial Sequence
<220> FEATURE:
```

```
<223> OTHER INFORMATION: synthetic peptide construct

<400> SEQUENCE: 6

Lys Val Arg Ser Glu Leu Glu Glu Trp Leu Ala Ala Leu Glu Glu Leu
1               5                   10                  15

Ala Arg Glu Leu Leu Ala Arg Leu
            20

<210> SEQ ID NO 7
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 7

Lys Val Arg Ser Glu Leu Glu Glu Trp Leu Ala Ala Leu Arg Glu Leu
1               5                   10                  15

Ala Glu Arg Leu Leu Ala Glu Leu
            20

<210> SEQ ID NO 8
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 8

Glu Val Glu Ser Lys Leu Arg Glu Trp Leu Ala Ala Leu Glu Glu Leu
1               5                   10                  15

Ala Arg Glu Leu Leu Ala Arg Leu
            20

<210> SEQ ID NO 9
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 9

Glu Val Glu Ser Lys Leu Arg Glu Trp Leu Ala Ala Leu Arg Glu Leu
1               5                   10                  15

Ala Glu Arg Leu Leu Ala Glu Leu
            20

<210> SEQ ID NO 10
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 10

Glu Val Arg Ser Lys Leu Glu Glu Trp Leu Ala Ala Leu Glu Glu Leu
1               5                   10                  15

Ala Arg Arg Leu Leu Ala Glu Leu
            20

<210> SEQ ID NO 11
<211> LENGTH: 24
<212> TYPE: PRT
<213> ORGANISM: Artificial Sequence
```

```
<220> FEATURE:
<223> OTHER INFORMATION: synthetic peptide construct

<400> SEQUENCE: 11

Lys Val Glu Ser Glu Leu Arg Glu Trp Leu Ala Ala Leu Glu Glu Leu
1               5                   10                  15

Ala Arg Glu Leu Leu Ala Arg Leu
            20

<210> SEQ ID NO 12
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 12

Lys Val Glu Ser Glu Leu Arg Glu Trp Leu Ala Ala Leu Arg Glu Leu
1               5                   10                  15

Ala Glu Arg Leu Leu Ala Glu Leu
            20

<210> SEQ ID NO 13
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 13

Lys Val Arg Ser Glu Leu Glu Glu Trp Leu Ala Ala Leu Glu Glu Leu
1               5                   10                  15

Ala Arg Arg Leu Leu Ala Glu Leu
            20

<210> SEQ ID NO 14
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 14

Lys Val Glu Ser Lys Leu Arg Glu Trp Leu Ala Ala Leu Glu Glu Leu
1               5                   10                  15

Ala Arg Arg Leu Leu Ala Glu Leu
            20

<210> SEQ ID NO 15
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 15

Arg Val Glu Ser Glu Leu Arg Glu Trp Leu Ala Ala Leu Glu Glu Leu
1               5                   10                  15

Ala Arg Arg Leu Leu Ala Glu Leu
            20

<210> SEQ ID NO 16
<211> LENGTH: 24
<212> TYPE: PRT
```

```
<213> ORGANISM: Artificial Sequence
<220> FEATURE:
<223> OTHER INFORMATION: synthetic peptide construct

<400> SEQUENCE: 16

Leu Arg Ala Leu Leu Glu Glu Ala Leu Glu Arg Leu Ala Ala Leu Trp
 1               5                  10                  15

Glu Glu Leu Glu Ser Arg Val Lys
            20

<210> SEQ ID NO 17
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 17

Leu Arg Ala Leu Leu Glu Glu Ala Leu Glu Arg Leu Ala Ala Leu Trp
 1               5                  10                  15

Glu Arg Leu Lys Ser Glu Val Glu
            20

<210> SEQ ID NO 18
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 18

Leu Arg Ala Leu Leu Glu Arg Ala Leu Glu Glu Leu Ala Ala Leu Trp
 1               5                  10                  15

Glu Glu Leu Lys Ser Arg Val Glu
            20

<210> SEQ ID NO 19
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 19

Leu Glu Ala Leu Leu Arg Glu Ala Leu Glu Arg Leu Ala Ala Leu Trp
 1               5                  10                  15

Glu Glu Leu Lys Ser Arg Val Glu
            20

<210> SEQ ID NO 20
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 20

Leu Arg Ala Leu Leu Glu Glu Ala Leu Glu Arg Leu Ala Ala Leu Trp
 1               5                  10                  15

Glu Arg Leu Glu Ser Glu Val Lys
            20

<210> SEQ ID NO 21
<211> LENGTH: 24
```

```
<212> TYPE: PRT
<213> ORGANISM: Artificial Sequence
<220> FEATURE:
<223> OTHER INFORMATION: synthetic peptide construct

<400> SEQUENCE: 21

Leu Arg Ala Leu Leu Glu Arg Ala Leu Glu Glu Leu Ala Ala Leu Trp
1               5                   10                  15

Glu Glu Leu Glu Ser Arg Val Lys
            20

<210> SEQ ID NO 22
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 22

Leu Glu Ala Leu Leu Arg Glu Ala Leu Glu Arg Leu Ala Ala Leu Trp
1               5                   10                  15

Glu Glu Leu Glu Ser Arg Val Lys
            20

<210> SEQ ID NO 23
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 23

Leu Arg Ala Leu Leu Glu Arg Ala Leu Glu Glu Leu Ala Ala Leu Trp
1               5                   10                  15

Glu Arg Leu Lys Ser Glu Val Glu
            20

<210> SEQ ID NO 24
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 24

Leu Glu Ala Leu Leu Arg Glu Ala Leu Glu Arg Leu Ala Ala Leu Trp
1               5                   10                  15

Glu Arg Leu Lys Ser Glu Val Glu
            20

<210> SEQ ID NO 25
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 25

Leu Glu Ala Leu Leu Arg Arg Ala Leu Glu Glu Leu Ala Ala Leu Trp
1               5                   10                  15

Glu Glu Leu Lys Ser Arg Val Glu
            20

<210> SEQ ID NO 26
```

```
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 26

Leu Arg Ala Leu Leu Glu Arg Ala Leu Glu Glu Leu Ala Ala Leu Trp
1               5                   10                  15

Glu Arg Leu Glu Ser Glu Val Lys
            20

<210> SEQ ID NO 27
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 27

Leu Glu Ala Leu Leu Arg Glu Ala Leu Glu Arg Leu Ala Ala Leu Trp
1               5                   10                  15

Glu Arg Leu Glu Ser Glu Val Lys
            20

<210> SEQ ID NO 28
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 28

Leu Glu Ala Leu Leu Arg Arg Ala Leu Glu Glu Leu Ala Ala Leu Trp
1               5                   10                  15

Glu Glu Leu Glu Ser Arg Val Lys
            20

<210> SEQ ID NO 29
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 29

Leu Glu Ala Leu Leu Arg Arg Ala Leu Glu Glu Leu Ala Ala Leu Trp
1               5                   10                  15

Glu Arg Leu Lys Ser Glu Val Glu
            20

<210> SEQ ID NO 30
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 30

Leu Glu Ala Leu Leu Arg Arg Ala Leu Glu Glu Leu Ala Ala Leu Trp
1               5                   10                  15

Glu Arg Leu Glu Ser Glu Val Lys
            20
```

```
<210> SEQ ID NO 31
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 31

Glu Val Arg Ser Lys Leu Glu Glu Trp Leu Ala Ala Leu Arg Glu Leu
1               5                   10                  15

Ala Glu Glu Leu Leu Ala Arg Leu
            20

<210> SEQ ID NO 32
<211> LENGTH: 24
<212> TYPE: PRT
<213> ORGANISM: Artificial Sequence
<220> FEATURE:
<223> OTHER INFORMATION: synthetic peptide construct

<400> SEQUENCE: 32

Leu Arg Ala Leu Leu Glu Glu Ala Leu Glu Arg Leu Ala Ala Leu Trp
1               5                   10                  15

Glu Glu Leu Lys Ser Arg Val Glu
            20

<210> SEQ ID NO 33
<211> LENGTH: 26
<212> TYPE: PRT
<213> ORGANISM: Artificial Sequence
<220> FEATURE:
<223> OTHER INFORMATION: synthetic peptide construct ATI-5261

<400> SEQUENCE: 33

Glu Val Arg Ser Lys Leu Glu Glu Trp Phe Ala Ala Phe Arg Glu Phe
1               5                   10                  15

Ala Glu Glu Phe Leu Ala Arg Leu Lys Ser
            20                  25

<210> SEQ ID NO 34
<211> LENGTH: 26
<212> TYPE: PRT
<213> ORGANISM: Artificial Sequence
<220> FEATURE:
<223> OTHER INFORMATION: synthetic peptide construct T5657-10

<400> SEQUENCE: 34

Lys Val Glu Ser Glu Leu Arg Glu Trp Phe Ala Ala Phe Glu Lys Phe
1               5                   10                  15

Ala Arg Arg Phe Leu Ala Glu Leu Glu Ser
            20                  25

<210> SEQ ID NO 35
<211> LENGTH: 26
<212> TYPE: PRT
<213> ORGANISM: Artificial Sequence
<220> FEATURE:
<223> OTHER INFORMATION: synthetic peptide construct T6023-2

<400> SEQUENCE: 35

Lys Val Glu Ser Glu Leu Arg Glu Trp Leu Ala Ala Leu Glu Lys Leu
1               5                   10                  15

Ala Arg Arg Leu Leu Ala Glu Leu Glu Ser
            20                  25
```

<210> SEQ ID NO 36
<211> LENGTH: 24
<212> TYPE: PRT
<213> ORGANISM: Artificial Sequence
<220> FEATURE:
<223> OTHER INFORMATION: synthetic peptide construct T5766-5

<400> SEQUENCE: 36

Glu Val Arg Ser Lys Leu Glu Glu Trp Phe Ala Ala Phe Arg Glu Phe
1               5                   10                  15

Ala Glu Glu Phe Leu Ala Arg Leu
            20

<210> SEQ ID NO 37
<211> LENGTH: 26
<212> TYPE: PRT
<213> ORGANISM: Artificial Sequence
<220> FEATURE:
<223> OTHER INFORMATION: synthetic peptide construct T5594-4

<400> SEQUENCE: 37

Glu Val Arg Ser Lys Leu Glu Glu Trp Phe Ala Ala Phe Arg Glu Phe
1               5                   10                  15

Ala Glu Glu Phe Leu Ala Arg Leu Asn Ser
            20                  25

<210> SEQ ID NO 38
<211> LENGTH: 26
<212> TYPE: PRT
<213> ORGANISM: Artificial Sequence
<220> FEATURE:
<223> OTHER INFORMATION: synthetic peptide construct T5594-5

<400> SEQUENCE: 38

Glu Val Lys Ser Lys Leu Glu Glu Trp Phe Ala Ala Phe Lys Glu Phe
1               5                   10                  15

Ala Glu Glu Phe Leu Ala Lys Leu Lys Ser
            20                  25

<210> SEQ ID NO 39
<211> LENGTH: 26
<212> TYPE: PRT
<213> ORGANISM: Artificial Sequence
<220> FEATURE:
<223> OTHER INFORMATION: synthetic peptide construct T5594-6

<400> SEQUENCE: 39

Glu Val Glu Ser Lys Leu Arg Glu Trp Phe Ala Ala Phe Glu Glu Phe
1               5                   10                  15

Ala Arg Glu Phe Leu Ala Arg Leu Lys Ser
            20                  25

<210> SEQ ID NO 40
<211> LENGTH: 26
<212> TYPE: PRT
<213> ORGANISM: Artificial Sequence
<220> FEATURE:
<223> OTHER INFORMATION: synthetic peptide construct T5594-7

```
<400> SEQUENCE: 40

Glu Val Glu Ser Lys Leu Arg Glu Trp Phe Ala Ala Phe Arg Glu Phe
1               5                   10                  15

Ala Glu Glu Phe Leu Ala Arg Leu Lys Ser
                20                  25
```